United States Patent
Yang et al.

(10) Patent No.: US 10,787,477 B2
(45) Date of Patent: Sep. 29, 2020

(54) SOLID FORM OF 4'-THIO-2'-FLUORONUCLEOSIDE PHOSPHAMIDE COMPOUND AND PREPARATION METHOD THEREFOR AND USE THEREOF

(71) Applicant: SICHUAN KELUN-BIOTECH BIOPHARMACEUTICAL CO., LTD., Chengdu, Sichuan (CN)

(72) Inventors: Chengxi Yang, Sichuan (CN); Yufeng Liang, Sichuan (CN); Jiangfeng Zhou, Sichuan (CN); Jianhua Ge, Sichuan (CN); Qiang Tian, Sichuan (CN); Mingliang Zhao, Sichuan (CN); Hong Zeng, Sichuan (CN); Fulu Zhao, Sichuan (CN); Jianfeng Han, Sichuan (CN); Lichun Wang, Sichuan (CN); Jingyi Wang, Sichuan (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 0 days.

(21) Appl. No.: 16/343,846

(22) PCT Filed: Dec. 15, 2017

(86) PCT No.: PCT/CN2017/116396
§ 371 (c)(1),
(2) Date: Apr. 22, 2019

(87) PCT Pub. No.: WO2018/113592
PCT Pub. Date: Jun. 28, 2018

(65) Prior Publication Data
US 2019/0241603 A1    Aug. 8, 2019

(30) Foreign Application Priority Data

Dec. 22, 2016 (CN) .......................... 2016 1 1199468

(51) Int. Cl.
| C07H 19/10 | (2006.01) |
| C07H 1/06 | (2006.01) |
| A61P 35/00 | (2006.01) |
| A61P 31/12 | (2006.01) |
| A61K 31/7068 | (2006.01) |

(52) U.S. Cl.
CPC ......... C07H 19/10 (2013.01); A61K 31/7068 (2013.01); A61P 31/12 (2018.01); A61P 35/00 (2018.01); C07H 1/06 (2013.01); C07B 2200/13 (2013.01)

(58) Field of Classification Search
CPC ...... C07H 19/10; C07H 1/06; A61K 31/7068; A61P 35/00; A61P 31/12
See application file for complete search history.

(56) References Cited

U.S. PATENT DOCUMENTS

| 5,128,458 A | 7/1992 | Montgomery et al. |
| 6,147,058 A | 11/2000 | Yoshimura et al. |
| 2014/0364446 A1* | 12/2014 | Dukhan ............... A61K 31/506 514/263.23 |
| 2017/0233429 A1* | 8/2017 | Kuniyoshi ......... A61K 31/7068 514/86 |

FOREIGN PATENT DOCUMENTS

| WO | 2014197578 A1 | 12/2014 |
| WO | 2016068341 A1 | 5/2016 |
| WO | 2016155593 A1 | 10/2016 |

OTHER PUBLICATIONS

Zajchowski D.A. et al., "Anti-tumor efficacy of the nucleoside analog 1-(2-deoxy-2-fluoro-4-thio-Beta-D-arabinofuranosyl) cytosine (4'-thio-FAC) in human pancreatic and ovarian tumor xenograft models", Publication of the International Union Against Cancer, 114, Wiley-Liss, Inc., 2005, pp. 1002-1009.

Miura, S. et al., "Comparison of 1-(2-deoxy-2-fluoro-4-thio-Beta-D-arabinofuranosyl)cytosine with gemcitabine in its antitumor activity", Cancer Letters 144, Elsevier Science Ireland Ltd., 1999, pp. 177-182.

(Continued)

*Primary Examiner* — Jonathan S Lau
(74) *Attorney, Agent, or Firm* — Rothwell, Figg, Ernst & Manbeck, P.C.

(57) ABSTRACT

The present invention relates to a solid form of a compound of Formula (I), a method for preparing the solid form, a pharmaceutical composition comprising the solid form, and the use of the solid form in the treatment of a disease involving abnormal cell proliferation or a viral infectious disease.

Formula (I)

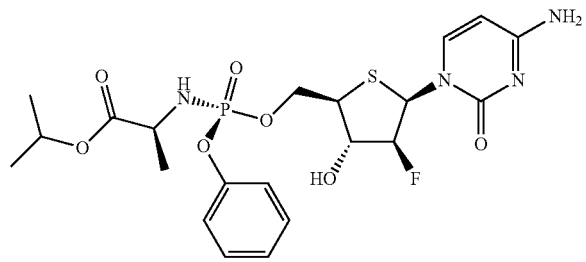

26 Claims, 8 Drawing Sheets

(56) References Cited

OTHER PUBLICATIONS

Wu, W. et al., "Synthesis and Biological Activity of a Gemcitabine Phoshoramidate Prodrug", J.Med. Chem. 2007, 50, pp. 3743-3746.
Rooseboom, M. et al., "Enzyme-Catalyzed Activation of Anticancer Prodrugs", Pharmacological Reviews, vol. 56, Vo. 1, 2004, pp. 53-102.
Xu, G. et al., "Strategies for Enzyme/Prodrug Cancer Therapy", Clinical Cancer Research, vol. 7, Nov. 2001, pp. 3314-3324.
International Search Report with English Translation issued in Application No. PCT/CN2017/116396 dated Mar. 21, 2018, 5 pages.

\* cited by examiner

SOLID FORM OF 4'-THIO-2'-FLUORONUCLEOSIDE PHOSPHAMIDE COMPOUND AND PREPARATION METHOD THEREFOR AND USE THEREOF

CROSS REFERENCE TO RELATED APPLICATION

This application is a 35 U.S.C. § 371 National Stage of International Application No. PCT/CN2017/116396, filed 15 Dec. 2017, designating the United States and claiming priority to Chinese application No. 201611199468.3 filed on 22 Dec. 2016. Each application is incorporated herein by reference in its entirety.

FIELD OF THE INVENTION

The present invention relates to a solid form of (S)-isopropyl 2-(((S)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate (hereinafter referred to as "the compound of Formula (I)"), a method for preparing the solid form, a pharmaceutical composition comprising the solid form, and the use of the solid form for the treatment of an abnormal cell proliferative disease or a viral infectious disease.

BACKGROUND OF THE INVENTION

Artificially synthesized nucleoside analogues are an important class of chemotherapeutic drugs for tumor, and are normally referred to as antimetabolites, such as gemcitabine, azacitidine, decitabine, cytarabine, fludarabine, cladribine, 6-azauridine, tiazofurine and atromide, etc. already available on the market. The mechanism is mainly inhibiting the synthesis of DNA and RNA through affecting the enzymatic system of tumor cells.

4'-thionucleoside refers to a nucleoside analogue with the oxygen atom in the furanose ring replaced by a sulfur atom. The synthetic process for 4'-thionucleosides is long and difficult, which greatly limits the study of such compounds. U.S. Pat. No. 6,147,058 discloses a 4'-thionucleoside compound which exhibits inhibitory activity in a colon cancer model in a nude mouse model. This compound is shown to have a better effect in inhibiting tumor growth with less toxicity than that of gemcitabine (Cancer Let. 1999, 144, 177-182). This compound also inhibits pancreatic and ovarian cancer in a nude mouse model, and its inhibitory activity and safety are superior to those of gemcitabine (Int. J. Cancer, 2005, 114, 1002-1009). U.S. Pat. Nos. 5,128,458 and 5,128,458 disclose a 2',3'-dideoxy-4'-thioribonucleotide with good effects in the treatment of both a viral infectious disease (such as HIV, hepatitis B or C) and an abnormal cell proliferative disease.

So far, problems such as low oral bioavailability, fast metabolism, multiple adverse effects and prone to drug resistance, etc. having been encountered in the development of 4'-thionucleoside drugs make them difficult to be marketed. A prodrug approach has been employed to overcome such problems of the thionucleoside drugs. Now a lot of pharmaceutical companies are still working in developing methods for treating cancers by using other prodrugs (G. Xu, H. L. McLeod, Clin. Cancer Res., 2001, 7, 3314-3324; M. Rooseboom, J. N. M. Commandeur, N. P. E. Vermeulen, Pharmacol. Rev., 2004, 56, 53-102; W. D. Wu, J. Sigmond, G. J. Peters, R. F. Borch, J. Med. Chem. 2007, 50, 3743-3746).

Therefore, finding a novel 4'-thio-2'-fluoronucleoside phosphoramide compound with excellent physicochemical properties, high bioavailability and/or less prone to drug resistance, and developing a crystalline form thereof suitable for the preparation of a pharmaceutical preparation is urgently needed in the medical field.

SUMMARY OF THE INVENTION

An aspect of the present invention provides crystalline forms of the compound of Formula (I) ((S)-isopropyl 2-(((S)-(((2R,3S,4S,5R)-5-(4-amino-2-oxopyrimidin-1(2H)-yl)-4-fluoro-3-hydroxytetrahydrothio-phen-2-yl)methoxy)(phenoxy)phosphoryl)amino)propanoate):

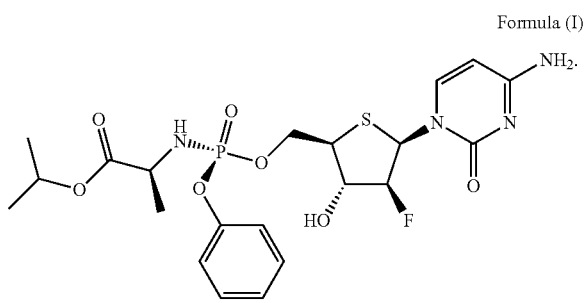 [SMILES: CC(C)OC(=O)[C@H](C)N[P@](=O)(OC[C@H]1S[C@@H](n2ccc(N)nc2=O)[C@@H](F)[C@@H]1O)Oc1ccccc1]

Formula (I)

The preferred crystalline forms of the present invention not only have an excellent effect in preventing or treating an abnormal cell proliferative disease or a viral infectious disease, but also have other advantages. For example, the preferred crystalline forms of the compound of Formula (I) of the present invention have excellent physical properties (including solubility, dissolution rate, light resistance, low hygroscopicity, high temperature resistance, high humidity resistance, fluidity, and the like), and the preferred crystalline forms of the present invention may have superior properties in terms of bioavailability, physical and/or chemical stability, and ease of preparation. The preferred crystalline forms of the present invention have good powder properties, are more suitable and convenient for mass production and for forming a formulation, can reduce irritation and enhance absorption, solve problems in metabolic rates, significantly decrease toxicity resulted from drug accumulation, improve safety, and effectively ensure the quality and efficacy of the pharmaceutical products.

The preferred crystalline forms of the compound of Formula (I) of the present invention exhibit good chemical and thermal stability, and thus are more advantageous for sufficient dissolution upon preparing formulations and administration thereof, and can retain adequate biological activity. Furthermore, the preferred crystalline forms of the compound of Formula (I) of the present invention have high bioavailability, and provide a therapeutically effective dosage of the compound of Formula (I) in vivo.

The preferred crystalline forms of the compound of Formula (I) of the present invention exhibit bare or little degradation during storage or transportation at ambient temperature, and the preferred crystalline forms of the compound of Formula (I) of the present invention melted or desolvated at above 50° C. in differential scanning calorimetry (DSC) analysis. This property renders the preferred crystalline forms of the present invention more suitable for standard processes of preparing a formulation.

The preferred crystalline forms of the compound of Formula (I) of the present invention were milled and then passed through 500 μm and 250 μm sieves to make a fine powder, and X-ray powder diffraction (XRPD) detection showed no change of the crystalline forms. This indicates that the preferred crystalline forms of the present invention have good stability, are easy to prepare, and are more suitable for the preparation of formulations.

Analyses using anti-solvent addition method showed that the preferred crystalline forms of the compound of Formula (I) of the present invention are more stable in aqueous pharmaceutical preparations, and thus the preferred crystalline forms of the present invention are more advantageous to be developed as a controlled release preparation or a sustained-release preparation.

The preferred crystalline forms of the compound of Formula (I) of the present invention have good photostability, ensuring the reliability of the crystalline forms (e.g., crystalline form A) during storage and transportation, thereby ensuring the safety of the drug. Furthermore, the crystalline forms (e.g., crystalline form A) do not require special packaging treatment to prevent from the effects of light, thereby reducing costs. The crystalline forms (e.g., crystalline form A) do not degrade by the effects of light, thereby improving the safety of the drug and sustain the efficacy upon long-term storage. A patient taking the crystalline forms (e.g., crystalline form A) would not develop a photosensitivity reaction due to exposure to sunlight.

The preferred crystalline forms of the compound of Formula (I) of the present invention have good fluidity and particle shape, as well as significantly improved stickiness, which can significantly reduce the filtration time, shorten the production cycle, and save costs during the formulation processes.

Another aspect of the present invention provides a method for the preparation of the crystalline forms of the present invention, selected from the group consisting of a gas-liquid permeation method, a room temperature slow volatilization method, a polymer induced crystallization method, a gas-solid permeation method, a slow cooling method, an anti-solvent addition method, a room temperature suspension stirring method and a high temperature suspension stirring method.

Another aspect of the present invention provides a pharmaceutical composition comprising any one or more of the crystalline forms of the present invention and one or more pharmaceutically acceptable carriers.

Another aspect of the present invention provides use of the crystalline forms of the present invention in the manufacture of a medicament for the prevention or treatment of an abnormal cell proliferative disease or a viral infectious disease.

DETAILED DESCRIPTION OF THE INVENTION

Crystalline Form and Preparation Method Therefor

In an embodiment, the present invention provides crystalline form A of the compound of Formula (I), and the crystalline form A has an XRPD pattern comprising characteristic peaks at diffraction angles (2θ) of about 10.5±0.2°, 13.5±0.2° and 17.9±0.2°.

In a preferred embodiment, crystalline form A of the compound of Formula (I) has an XRPD pattern comprising characteristic peaks at diffraction angles (2θ) of about 10.5±0.2°, 13.5±0.2°, 15.8±0.2°, 17.9±0.2°, 18.3±0.2° and 21.3±0.2°.

In a more preferred embodiment, crystalline form A of the compound of Formula (I) has an XRPD pattern comprising characteristic peaks at diffraction angles (2θ) of about 10.5±0.2°, 13.5±0.2°, 15.8±0.2°, 17.9±0.2°, 18.3±0.2°, 21.3±0.2°, 22.3±0.2°, 24.2±0.2° and 26.8±0.2°.

In a more preferred embodiment, crystalline form A of the compound of Formula (I) has an XRPD pattern comprising peaks at the following diffraction angles (2θ):

| 2θ (°) ± 0.2° |
| --- |
| 5.3 |
| 7.8 |
| 8.7 |
| 10.5 |
| 13.5 |
| 15.2 |
| 15.8 |
| 16.4 |
| 17.4 |
| 17.9 |
| 18.3 |
| 19.2 |
| 19.9 |
| 20.3 |
| 20.6 |
| 21.3 |
| 22.3 |
| 23.3 |
| 23.6 |
| 24.2 |
| 25.0 |
| 25.8 |
| 26.4 |
| 26.8 |
| 27.9 |
| 28.6 |
| 28.9 |
| 30.2 |

In a more preferred embodiment, crystalline form A of the compound of Formula (I) has an XRPD pattern comprising peaks at the following diffraction angles (2θ):

| 2θ (°) ± 0.2° | Intensity % |
| --- | --- |
| 5.3 | 29.7 |
| 7.8 | 5.9 |
| 8.7 | 8.3 |
| 10.5 | 100.0 |
| 13.5 | 21.8 |
| 15.2 | 1.9 |
| 15.8 | 12.2 |
| 16.4 | 4.6 |
| 17.4 | 2.4 |
| 17.9 | 27.8 |
| 18.3 | 6.2 |
| 19.2 | 2.7 |
| 19.9 | 1.1 |
| 20.3 | 0.8 |
| 20.6 | 3.1 |
| 21.3 | 18.6 |
| 22.3 | 5.1 |
| 23.3 | 2.9 |
| 23.6 | 3.9 |
| 24.2 | 11.1 |
| 25.0 | 1.4 |
| 25.8 | 2.0 |
| 26.4 | 5.0 |
| 26.8 | 6.1 |
| 27.9 | 4.1 |
| 28.6 | 2.3 |

-continued

| 2θ (°) ± 0.2° | Intensity % |
|---|---|
| 28.9 | 4.9 |
| 30.2 | 1.0 |

In a more preferred embodiment, crystalline form A of the compound of Formula (I) has an XRPD pattern comprising peaks at the following diffraction angles (2θ):

| 2θ (°) ± 0.2° | Interplanar spacing (d-spacing) | Intensity % |
|---|---|---|
| 5.3 | 16.8 | 29.7 |
| 7.8 | 11.3 | 5.9 |
| 8.7 | 10.2 | 8.3 |
| 10.5 | 8.4 | 100.0 |
| 13.5 | 6.6 | 21.8 |
| 15.2 | 5.8 | 1.9 |
| 15.8 | 5.6 | 12.2 |
| 16.4 | 5.4 | 4.6 |
| 17.4 | 5.1 | 2.4 |
| 17.9 | 5.0 | 27.8 |
| 18.3 | 4.9 | 6.2 |
| 19.2 | 4.6 | 2.7 |
| 19.9 | 4.5 | 1.1 |
| 20.3 | 4.4 | 0.8 |
| 20.6 | 4.3 | 3.1 |
| 21.3 | 4.2 | 18.6 |
| 22.3 | 4.0 | 5.1 |
| 23.3 | 3.8 | 2.9 |
| 23.6 | 3.8 | 3.9 |
| 24.2 | 3.7 | 11.1 |
| 25.0 | 3.6 | 1.4 |
| 25.8 | 3.5 | 2.0 |
| 26.4 | 3.4 | 5.0 |
| 26.8 | 3.3 | 6.1 |
| 27.9 | 3.2 | 4.1 |
| 28.6 | 3.1 | 2.3 |
| 28.9 | 3.1 | 4.9 |
| 30.2 | 3.0 | 1.0 |

In a more preferred embodiment, crystalline form A of the compound of Formula (I) has an XRPD pattern comprising peaks at diffraction angles (2θ) essentially the same as shown in FIG. 1. In the most preferred embodiment, crystalline form A of the compound of Formula (I) has XRPD peak positions essentially the same as shown in FIG. 1.

In a preferred embodiment, crystalline form A of the compound of Formula (I) has a DSC graph comprising a characteristic peak at about 155.7±0.2° C. (the onset temperature).

In a more preferred embodiment, crystalline form A of the compound of Formula (I) has a DSC graph comprising a characteristic peak at a temperature essentially the same as shown in FIG. 2. In the most preferred embodiment, the characteristic peak position in the DSC graph of crystalline form A of the compound of Formula (I) is essentially the same as shown in FIG. 2.

In a preferred embodiment, crystalline form A of the compound of Formula (I) is in an unsolvated form. In a more preferred embodiment, crystalline form A of the compound of Formula (I) is an anhydrous crystalline form.

In another embodiment, the present invention provides crystalline form B of the compound of Formula (I), and the crystalline form B has an XRPD pattern comprising characteristic peaks at diffraction angles (2θ) of about 7.0±0.2°, 14.0±0.2° and 21.1±0.2°.

In a preferred embodiment, the crystalline form B of the compound of Formula (I) has an XRPD pattern comprising characteristic peaks at diffraction angles (2θ) of about 6.2±0.2°, 7.0±0.2°, 13.2±0.2°, 14.0±0.2°, 21.1±0.2° and 26.2±0.2°.

In a more preferred embodiment, the crystalline form B of the compound of Formula (I) has an XRPD pattern comprising characteristic peaks at diffraction angles (2θ) of about 6.2±0.2°, 7.0±0.2°, 9.3±0.2°, 13.2±0.2°, 14.0±0.2°, 15.5±0.2°, 18.7±0.2°, 21.1±0.2° and 26.2±0.2°.

In a more preferred embodiment, the crystalline form B of the compound of Formula (I) has an XRPD pattern comprising peaks at the following diffraction angles (2θ):

| 2θ (°) ± 0.2° |
|---|
| 6.2 |
| 7.0 |
| 9.3 |
| 11.8 |
| 12.5 |
| 13.2 |
| 14.0 |
| 14.7 |
| 15.5 |
| 16.5 |
| 17.4 |
| 18.7 |
| 19.7 |
| 21.1 |
| 22.9 |
| 23.4 |
| 23.7 |
| 24.3 |
| 26.2 |
| 26.5 |
| 27.5 |
| 29.4 |
| 33.3 |
| 35.2 |

In a more preferred embodiment, the crystalline form B of the compound of Formula (I) has an XRPD pattern comprising peaks at the following diffraction angles (2θ):

| 2θ (°) ± 0.2° | Intensity % |
|---|---|
| 6.2 | 100.0 |
| 7.0 | 15.3 |
| 9.3 | 36.7 |
| 11.8 | 3.5 |
| 12.5 | 10.1 |
| 13.2 | 13.3 |
| 14.0 | 31.2 |
| 14.7 | 2.7 |
| 15.5 | 8.8 |
| 16.5 | 5.6 |
| 17.4 | 6.8 |
| 18.7 | 9.8 |
| 19.7 | 10.4 |
| 21.1 | 52.5 |
| 22.9 | 4.0 |
| 23.4 | 8.5 |
| 23.7 | 5.2 |
| 24.3 | 5.9 |
| 26.2 | 10.0 |
| 26.5 | 12.7 |
| 27.5 | 5.1 |
| 29.4 | 1.0 |
| 33.3 | 1.7 |
| 35.2 | 2.6 |

In a more preferred embodiment, the crystalline form B of the compound of Formula (I) has an XRPD pattern comprising peaks at the following diffraction angles (2θ):

| 2θ (°) ± 0.2° | Interplanar spacing (d-spacing) | Intensity % |
| --- | --- | --- |
| 6.2 | 14.1 | 100.0 |
| 7.0 | 12.6 | 15.3 |
| 9.3 | 9.5 | 36.7 |
| 11.8 | 7.5 | 3.5 |
| 12.5 | 7.1 | 10.1 |
| 13.2 | 6.7 | 13.3 |
| 14.0 | 6.3 | 31.2 |
| 14.7 | 6.0 | 2.7 |
| 15.5 | 5.7 | 8.8 |
| 16.5 | 5.4 | 5.6 |
| 17.4 | 5.1 | 6.8 |
| 18.7 | 4.7 | 9.8 |
| 19.7 | 4.5 | 10.4 |
| 21.1 | 4.2 | 52.5 |
| 22.9 | 3.9 | 4.0 |
| 23.4 | 3.8 | 8.5 |
| 23.7 | 3.8 | 5.2 |
| 24.3 | 3.7 | 5.9 |
| 26.2 | 3.4 | 10.0 |
| 26.5 | 3.4 | 12.7 |
| 27.5 | 3.2 | 5.1 |
| 29.4 | 3.0 | 1.0 |
| 33.3 | 2.7 | 1.7 |
| 35.2 | 2.6 | 2.6 |

In a more preferred embodiment, the crystalline form B of the compound of Formula (I) has an XRPD pattern comprising peaks at diffraction angles (2θ) essentially the same as shown in FIG. 3. In the most preferred embodiment, the crystalline form B of the compound of Formula (I) has XRPD peak positions essentially the same as shown in FIG. 3.

In a preferred embodiment, the crystalline form B of the compound of Formula (I) has a DSC graph comprising a characteristic peak at about 125.3±0.2° C. (the onset temperature).

In a more preferred embodiment, the crystalline form B of the compound of Formula (I) has a DSC graph comprising a characteristic peak at a temperature essentially the same as shown in FIG. 4. In the most preferred embodiment, the characteristic peak position in the DSC graph of the crystalline form B of the compound of Formula (I) is essentially the same as shown in FIG. 4.

In a preferred embodiment, the crystalline form B of the compound of Formula (I) is in an unsolvated form. In a more preferred embodiment, the crystalline form B of the compound of Formula (I) is an anhydrous crystalline form.

In another embodiment, the present invention provides crystalline form C of the compound of Formula (I), and the crystalline form C has an XRPD pattern comprising characteristic peaks at diffraction angles (2θ) of about 8.6±0.2°, 17.2±0.2° and 21.0±0.2°.

In a preferred embodiment, the crystalline form C of the compound of Formula (I) has an XRPD pattern comprising characteristic peaks at diffraction angles (2θ) of about 8.6±0.2°, 10.1±0.2°, 14.4±0.2°, 17.2±0.2°, 18.0±0.2° and 21.0±0.2°.

In a more preferred embodiment, the crystalline form C of the compound of Formula (I) has an XRPD pattern comprising characteristic peaks at diffraction angles (2θ) of about 8.6±0.2°, 10.1±0.2°, 14.4±0.2°, 17.2±0.2°, 18.0±0.2°, 18.6±0.2°, 21.0±0.2°, 24.9±0.2° and 26.0±0.2°.

In a more preferred embodiment, the crystalline form C of the compound of Formula (I) has an XRPD pattern comprising peaks at the following diffraction angles (2θ):

| 2θ (°) ± 0.2° |
| --- |
| 4.7 |
| 8.6 |
| 10.1 |
| 13.3 |
| 14.1 |
| 14.4 |
| 16.1 |
| 16.6 |
| 17.2 |
| 18.0 |
| 18.6 |
| 19.7 |
| 21.0 |
| 24.9 |
| 26.0 |
| 26.8 |
| 29.3 |

In a more preferred embodiment, the crystalline form C of the compound of Formula (I) has an XRPD pattern comprising peaks at the following diffraction angles (2θ):

| 2θ (°) ± 0.2° | Intensity % |
| --- | --- |
| 4.7 | 0.8 |
| 8.6 | 100.0 |
| 10.1 | 5.2 |
| 13.3 | 2.0 |
| 14.1 | 3.3 |
| 14.4 | 5.2 |
| 16.1 | 2.8 |
| 16.6 | 2.6 |
| 17.2 | 12.4 |
| 18.0 | 6.0 |
| 18.6 | 4.2 |
| 19.7 | 1.7 |
| 21.0 | 17.1 |
| 24.9 | 3.9 |
| 26.0 | 4.4 |
| 26.8 | 1.8 |
| 29.3 | 2.6 |

In a more preferred embodiment, the crystalline form C of the compound of Formula (I) has an XRPD pattern comprising peaks at the following diffraction angles (2θ):

| 2θ (°) ± 0.2° | Interplanar spacing (d-spacing) | Intensity % |
| --- | --- | --- |
| 4.7 | 18.7 | 0.8 |
| 8.6 | 10.3 | 100.0 |
| 10.1 | 8.8 | 5.2 |
| 13.3 | 6.7 | 2.0 |
| 14.1 | 6.3 | 3.3 |
| 14.4 | 6.2 | 5.2 |
| 16.1 | 5.5 | 2.8 |
| 16.6 | 5.3 | 2.6 |
| 17.2 | 5.2 | 12.4 |
| 18.0 | 4.9 | 6.0 |
| 18.6 | 4.8 | 4.2 |
| 19.7 | 4.5 | 1.7 |
| 21.0 | 4.2 | 17.1 |
| 24.9 | 3.6 | 3.9 |
| 26.0 | 3.4 | 4.4 |
| 26.8 | 3.3 | 1.8 |
| 29.3 | 3.0 | 2.6 |

In a more preferred embodiment, the crystalline form C of the compound of Formula (I) has an XRPD pattern comprising peaks at diffraction angles (2θ) essentially the same as shown in FIG. 5. In the most preferred embodiment, the crystalline form C of the compound of Formula (I) has XRPD peak positions essentially the same as shown in FIG. 5.

In another embodiment, the present invention provides crystalline form D of the compound of Formula (I), and the crystalline form D has an XRPD pattern comprising characteristic peaks at diffraction angles (2θ) of about 10.2±0.2°, 18.8±0.2° and 20.4±0.2°.

In a preferred embodiment, the crystalline form D of the compound of Formula (I) has an XRPD pattern comprising characteristic peaks at diffraction angles (2θ) of about 10.2±0.2°, 15.4±0.2°, 16.9±0.2°, 18.2±0.2°, 18.8±0.2° and 20.4±0.2°.

In a more preferred embodiment, the crystalline form D of the compound of Formula (I) has an XRPD pattern comprising characteristic peaks at diffraction angles (2θ) of about 10.2±0.2°, 14.3±0.2°, 15.4±0.2°, 16.9±0.2°, 18.2±0.2°, 18.8±0.2°, 20.4±0.2°, 25.0±0.2° and 28.6±0.2°.

In a more preferred embodiment, the crystalline form D of the compound of Formula (I) has an XRPD pattern comprising peaks at the following diffraction angles (2θ):

| 2θ (°) ± 0.2° |
| --- |
| 8.3 |
| 10.2 |
| 13.4 |
| 14.3 |
| 15.4 |
| 16.9 |
| 17.6 |
| 18.2 |
| 18.8 |
| 19.2 |
| 20.4 |
| 23.0 |
| 25.0 |
| 25.8 |
| 27.2 |
| 28.6 |
| 31.2 |

In a more preferred embodiment, the crystalline form D of the compound of Formula (I) has an XRPD pattern comprising peaks at the following diffraction angles (2θ):

| 2θ (°) ± 0.2° | Intensity % |
| --- | --- |
| 8.3 | 5.1 |
| 10.2 | 100.0 |
| 13.4 | 4.2 |
| 14.3 | 3.4 |
| 15.4 | 8.9 |
| 16.9 | 7.2 |
| 17.6 | 5.6 |
| 18.2 | 10.4 |
| 18.8 | 20.9 |
| 19.2 | 4.3 |
| 20.4 | 12.8 |
| 23.0 | 3.0 |
| 25.0 | 1.8 |
| 25.8 | 1.9 |
| 27.2 | 1.4 |
| 28.6 | 6.1 |
| 31.2 | 0.6 |

In a more preferred embodiment, the crystalline form D of the compound of Formula (I) has an XRPD pattern comprising peaks at the following diffraction angles (2θ):

| 2θ (°) ± 0.2° | Interplanar spacing (d-spacing) | Intensity % |
| --- | --- | --- |
| 8.3 | 10.7 | 5.1 |
| 10.2 | 8.7 | 100.0 |
| 13.4 | 6.6 | 4.2 |
| 14.3 | 6.2 | 3.4 |
| 15.4 | 5.8 | 8.9 |
| 16.9 | 5.3 | 7.2 |
| 17.6 | 5.0 | 5.6 |
| 18.2 | 4.9 | 10.4 |
| 18.8 | 4.7 | 20.9 |
| 19.2 | 4.6 | 4.3 |
| 20.4 | 4.5 | 12.8 |
| 23.0 | 3.9 | 3.0 |
| 25.0 | 3.6 | 1.8 |
| 25.8 | 3.4 | 1.9 |
| 27.2 | 3.3 | 1.4 |
| 28.6 | 3.1 | 6.1 |
| 31.2 | 2.9 | 0.6 |

In a more preferred embodiment, the crystalline form D of the compound of Formula (I) has an XRPD pattern comprising peaks at diffraction angles (2θ) essentially the same as shown in FIG. 6. In the most preferred embodiment, the crystalline form D of the compound of Formula (I) has XRPD peak positions essentially the same as shown in FIG. 6.

In a preferred embodiment, crystalline form D of the compound of Formula (I) of the present invention has a DSC graph comprising a characteristic peak at about 144.2±0.2° C. (the onset temperature).

In a more preferred embodiment, the crystalline form D of the compound of Formula (I) has a DSC graph comprising a characteristic peak at a temperature essentially the same as shown in FIG. 7. In the most preferred embodiment, the characteristic peak position in the DSC graph of the crystalline form D of the compound of Formula (I) is essentially the same as shown in FIG. 7.

In a preferred embodiment, the crystalline form D of the compound of Formula (I) of the present invention is in an unsolvated form. In a more preferred embodiment, the crystalline form D of the compound of Formula (I) of the present invention is an anhydrous crystalline form.

In another embodiment, the present invention provides crystalline form E of the compound of Formula (I), and the crystalline form E has an XRPD pattern comprising characteristic peaks at diffraction angles (2θ) of about 4.0±0.2°, 6.8±0.2° and 8.0±0.2°.

In a preferred embodiment, the crystalline form E of the compound of Formula (I) has an XRPD pattern comprising characteristic peaks at diffraction angles (2θ) of about 4.0±0.2°, 6.8±0.2°, 8.0±0.2°, 11.6±0.2°, 18.6±0.2° and 19.8±0.2°.

In a more preferred embodiment, the crystalline form E of the compound of Formula (I) has an XRPD pattern comprising characteristic peaks at diffraction angles (2θ) of about 4.0±0.2°, 6.8±0.2°, 8.0±0.2°, 11.6±0.2°, 18.6±0.2°, 19.8±0.2°, 23.8±0.2°, 29.6±0.2° and 33.9±0.2°.

In a more preferred embodiment, the crystalline form E of the compound of Formula (I) has an XRPD pattern comprising peaks at the following diffraction angles (2θ):

| 2θ (°) ± 0.2° |
| --- |
| 4.0 |
| 6.8 |
| 8.0 |
| 11.6 |

-continued

| 2θ (°) ± 0.2° |
|---|
| 18.6 |
| 19.8 |
| 23.8 |
| 29.6 |
| 33.9 |

In a more preferred embodiment, the crystalline form E of the compound of Formula (I) has an XRPD pattern comprising peaks at the following diffraction angles (2θ):

| 2θ (°) ± 0.2° | Intensity % |
|---|---|
| 4.0 | 100.0 |
| 6.8 | 83.9 |
| 8.0 | 84.9 |
| 11.6 | 27.8 |
| 18.6 | 26.8 |
| 19.8 | 31.3 |
| 23.8 | 16.2 |
| 29.6 | 0.5 |
| 33.9 | 1.1 |

In a more preferred embodiment, the crystalline form E of the compound of Formula (I) has an XRPD pattern comprising peaks at the following diffraction angles (2θ):

| 2θ (°) ± 0.2° | Interplanar spacing (d-spacing) | Intensity % |
|---|---|---|
| 4.0 | 21.9 | 100.0 |
| 6.8 | 13.0 | 83.9 |
| 8.0 | 11.0 | 84.9 |
| 11.6 | 7.7 | 27.8 |
| 18.6 | 4.8 | 26.8 |
| 19.8 | 4.5 | 31.3 |
| 23.8 | 3.7 | 16.2 |
| 29.6 | 3.0 | 0.5 |
| 33.9 | 2.7 | 1.1 |

In a more preferred embodiment, the crystalline form E of the compound of Formula (I) has an XRPD pattern comprising peaks at diffraction angles (2θ) essentially the same as shown in FIG. 8. In the most preferred embodiment, the crystalline form E of the compound of Formula (I) has XRPD peak positions essentially the same as shown in FIG. 8.

In a preferred embodiment, crystalline form E of the compound of Formula (I) of the present invention has a DSC graph comprising a characteristic peak at about 96.6±0.2° C. (the onset temperature).

In a more preferred embodiment, the crystalline form E of the compound of Formula (I) has a DSC graph comprising a characteristic peak at a temperature essentially the same as shown in FIG. 9. In the most preferred embodiment, the characteristic peak position in the DSC graph of the crystalline form E of the compound of Formula (I) is essentially the same as shown in FIG. 9.

In a preferred embodiment, crystalline form E of the compound of Formula (I) of the present application is a solvate formed by the compound of Formula (I) with tetrahydrofuran.

In another embodiment, the present invention provides crystalline form F of the compound of Formula (I), and the crystalline form F has an XRPD pattern comprising characteristic peaks at diffraction angles (2θ) of about 6.7±0.2°, 13.5±0.2° and 20.4±0.2°.

In a preferred embodiment, the crystalline form F of the compound of Formula (I) has an XRPD pattern comprising characteristic peaks at diffraction angles (2θ) of about 5.8±0.2°, 6.7±0.2°, 13.5±0.2°, 14.2±0.2°, 17.8±0.2° and 20.4±0.2°.

In a more preferred embodiment, the crystalline form F of the compound of Formula (I) has an XRPD pattern comprising characteristic peaks at diffraction angles (2θ) of about 5.8±0.2°, 6.7±0.2°, 9.4±0.2°, 11.7±0.2°, 13.5±0.2°, 14.2±0.2°, 17.8±0.2°, 20.4±0.2° and 27.3±0.2°.

In a more preferred embodiment, the crystalline form F of the compound of Formula (I) has an XRPD pattern comprising peaks at the following diffraction angles (2θ):

| 2θ (°) ± 0.2° |
|---|
| 3.1 |
| 5.8 |
| 6.7 |
| 9.4 |
| 10.5 |
| 11.7 |
| 13.5 |
| 14.2 |
| 14.9 |
| 15.6 |
| 17.1 |
| 17.8 |
| 19.3 |
| 20.4 |
| 20.5 |
| 24.0 |
| 24.5 |
| 25.4 |
| 26.5 |
| 27.3 |
| 29.1 |
| 30.9 |
| 32.7 |
| 34.3 |
| 36.2 |
| 37.1 |

In a more preferred embodiment, the crystalline form F of the compound of Formula (I) has an XRPD pattern comprising peaks at the following diffraction angles (2θ):

| 2θ (°) ± 0.2° | Intensity % |
|---|---|
| 3.1 | 23.9 |
| 5.8 | 23.0 |
| 6.7 | 61.8 |
| 9.4 | 7.9 |
| 10.5 | 8.0 |
| 11.7 | 6.6 |
| 13.5 | 94.9 |
| 14.2 | 10.1 |
| 14.9 | 1.8 |
| 15.6 | 2.3 |
| 17.1 | 9.1 |
| 17.8 | 9.3 |
| 19.3 | 4.9 |
| 20.4 | 100.0 |
| 20.5 | 92.4 |
| 24.0 | 10.3 |
| 24.5 | 5.5 |
| 25.4 | 6.6 |
| 26.5 | 3.9 |
| 27.3 | 4.4 |
| 29.1 | 1.2 |
| 30.9 | 0.6 |
| 32.7 | 0.7 |

-continued

| 2θ (°) ± 0.2° | Intensity % |
|---|---|
| 34.3 | 1.7 |
| 36.2 | 1.0 |
| 37.1 | 2.4 |

In a more preferred embodiment, the crystalline form F of the compound of Formula (I) has an XRPD pattern comprising peaks at the following diffraction angles (2θ):

| 2θ (°) ± 0.2° | Interplanar spacing (d-spacing) | Intensity % |
|---|---|---|
| 3.1 | 28.3 | 23.9 |
| 5.8 | 15.2 | 23.0 |
| 6.7 | 13.2 | 61.8 |
| 9.4 | 9.4 | 7.9 |
| 10.5 | 8.5 | 8.0 |
| 11.7 | 7.6 | 6.6 |
| 13.5 | 6.6 | 94.9 |
| 14.2 | 6.2 | 10.1 |
| 14.9 | 6.0 | 1.8 |
| 15.6 | 5.7 | 2.3 |
| 17.1 | 5.2 | 9.1 |
| 17.8 | 5.0 | 9.3 |
| 19.3 | 4.6 | 4.9 |
| 20.4 | 4.4 | 100.0 |
| 20.5 | 4.3 | 92.4 |
| 24.0 | 3.7 | 10.3 |
| 24.5 | 3.6 | 5.5 |
| 25.4 | 3.5 | 6.6 |
| 26.5 | 3.4 | 3.9 |
| 27.3 | 3.3 | 4.4 |
| 29.1 | 3.1 | 1.2 |
| 30.9 | 2.9 | 0.6 |
| 32.7 | 2.7 | 0.7 |
| 34.3 | 2.6 | 1.7 |
| 36.2 | 2.5 | 1.0 |
| 37.1 | 2.4 | 2.4 |

In a more preferred embodiment, the crystalline form F of the compound of Formula (I) has an XRPD pattern comprising peaks at diffraction angles (2θ) essentially the same as shown in FIG. 10. In the most preferred embodiment, the crystalline form F of the compound of Formula (I) has XRPD peak positions essentially the same as shown in FIG. 10.

In a preferred embodiment, crystalline form F of the compound of Formula (I) of the present invention has a DSC graph comprising a characteristic peak at about 121.9±0.2° C. (the onset temperature).

In a more preferred embodiment, the crystalline form F of the compound of Formula (I) has a DSC graph comprising a characteristic peak at a temperature essentially the same as shown in FIG. 11. In the most preferred embodiment, the characteristic peak position in the DSC graph of the crystalline form F of the compound of Formula (I) is essentially the same as shown in FIG. 11.

In a preferred embodiment, crystalline form F of the compound of Formula (I) of the present invention is a solvate formed by the compound of Formula (I) with tetrahydrofuran.

In an embodiment, the present invention further provides a method for the preparation of any one of crystalline forms A-F as mentioned above, and the method includes, but is not limited to, a gas-liquid permeation method, a room temperature slow volatilization method, a high polymer induced crystallization method, a gas-solid permeation method, a slow cooling method, an anti-solvent addition method, a room temperature suspension stirring method and a high temperature suspension stirring method, etc.

In some embodiments of the present invention, a crystalline form is prepared by a gas-liquid permeation method, comprising dissolving the compound of Formula (I) in a good solvent in a first vessel to form a clear solution (the solution may be filtered as needed to provide a clear solution), adding an anti-solvent to a second vessel, placing the open first vessel in the second vessel, sealing the second vessel and allowing it to stand, and filtering the precipitated solid to afford the crystalline form.

In some embodiments, the good solvent includes, but is not limited to, organic solvents, such as alcohols, ketones, hydrocarbons (including alkanes, halogenated alkanes, alkenes, alkynes, and aromatic hydrocarbons), ethers (including chain ethers and cyclic ethers (such as furans (including tetrahydrofurans) and dioxanes) and organic acids having 1 to 10 carbon atoms, etc., specifically such as acetone, acetic acid, methanol, ethanol, tetrahydrofuran or chloroform, or a mixed solvent formed by two or more of the above solvents.

In some embodiments, the anti-solvent includes, but is not limited to, organic solvents, such as ketones, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), esters and nitriles having 1 to 10 carbon atoms, such as dichloromethane, chloroform, methyl tert-butyl ether, toluene, n-hexane, acetonitrile, 2-methyltetrahydrofuran, ethyl acetate, butanone or the like, or a mixed solvent formed by two or more of the above solvents.

In some embodiments, the weight/volume ratio (mg/mL) of the compound of Formula (I) to the good solvent is about (10-50):1. In some embodiments, the volume ratio of the good solvent to the anti-solvent is 1:(2-10). In some embodiments, the sealing and standing of the second vessel can be carried out at room temperature. In some embodiments of the present invention, the method for preparing the crystalline form of the present invention and the results are exemplified as follows:

| Good solvent | Anti-solvent | Solid crystalline form |
|---|---|---|
| ethanol | 2-methyltetrahydrofuran | crystalline form B |
| chloroform | butanone | crystalline form B |

In some embodiments of the present invention, a crystalline form is prepared by a room temperature slow volatilization method, comprising dissolving the compound of Formula (I) in a solvent in a vessel to form a clear solution (the solution may be filtered as needed to provide a clear solution), sealing (e.g., with parafilm) the vessel while retaining a small hole or slit in the seal, allowing the clear solution to stand, and volatilizing the solvent, to afford the crystalline form.

In some embodiments, the solvent includes, but is not limited to, organic solvents, such as alcohols, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), ketones, nitriles or esters having 1 to 10 carbon atoms, specifically such as methanol, ethanol, isopropanol, trichloromethane (chloroform), tetrahydrofuran, acetone, methyl tert-butyl ether, ethyl acetate or acetonitrile, or a mixed solvent formed by two or more of the above solvents.

In some embodiments, the weight/volume ratio (mg/mL) of the compound of Formula (I) to the solvent is (5-20):1. In some embodiments, the standing can be carried out at room temperature. In some embodiments of the present invention, the method for preparing the crystalline form of the present invention and the results are exemplified as follows:

| Solvent | Solid crystalline form |
|---|---|
| ethanol | crystalline form B |
| chloroform | crystalline form D |
| isopropanol:acetonitrile (1:5) | crystalline form A |

In some embodiments of the present invention, a crystalline form is prepared by a high polymer induced crystallization method, comprising forming a clear solution of the compound of Formula (I) in a solvent in a vessel (the solution may be filtered as needed to provide a clear solution), adding a high polymer, sealing the vessel while retaining a small hole or slit in the seal, allowing the clear solution to stand, and volatilizing the solvent, to afford the crystalline form.

In some embodiments, the solvent includes, but is not limited to, organic solvents, such as alcohols, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), ketones, nitriles or esters having 1 to 10 carbon atoms, specifically such as methanol, ethanol, isopropanol, trichloromethane (chloroform), tetrahydrofuran, acetone, methyl tert-butyl ether, ethyl acetate, acetonitrile, or a mixed solvent formed by two or more of the above solvents.

In some embodiments, the high polymer may be a mixture of a plurality of high polymers (mixed high polymer), which may be mixed in any ratio, provided that it can be used to prepare the crystalline form.

In some embodiments, the mixed high polymer is, for example, mixed high polymer A: a mixture of polyvinylpyrrolidone, polyvinyl alcohol, polyvinyl chloride, polyvinyl acetate, hydroxypropyl methylcellulose, and methylcellulose. In some embodiments, the mixed high polymer is, for example, mixed high polymer B: a mixture of polycaprolactone, polyethylene glycol, polymethyl methacrylate, sodium alginate, and hydroxyethyl cellulose.

In some embodiments, the standing is carried out at room temperature. In some embodiments, the mixed high polymer is a mixture of each of the components in equal weights. In some embodiments, the weight ratio of the compound of Formula (I) to the mixed high polymer is (5-10):1. In some embodiments, the weight/volume ratio (mg/mL) of the compound of Formula (I) to the solvent is (5-20):1. In some embodiments of the present invention, the method for preparing the crystalline form of the present invention and the results are exemplified as follows:

| Solvent | High polymer | Solid crystalline form |
|---|---|---|
| acetone | mixed high polymer A | crystalline form B |
| acetonitrile/tetrahydrofuran, 1:5 | mixed high polymer B | crystalline form F |

In some embodiments of the present invention, a crystalline form is prepared by a gas-solid permeation method, comprising placing a first vessel containing the compound of Formula (I) in a second vessel containing a solvent, wherein the compound of Formula (I) in a solid form is not in direct contact with the solvent, sealing the second vessel, and obtaining the crystalline form upon standing.

In some embodiments, the solvent includes, but is not limited to, inorganic solvents (e.g., water) and organic solvents, such as ketones, hydrocarbons (including alkanes, halogenated alkanes, alkenes, alkynes and aromatic hydrocarbons), ethers (including chain ethers and cyclic ethers (such as furans (including tetrahydrofurans) and dioxanes)), nitriles and esters having 1 to 10 carbon atoms, such as dichloromethane, acetonitrile, tetrahydrofuran, acetone, ethyl acetate, methyl tert-butyl ether, toluene or chloroform.

In some embodiments, the weight/volume ratio (mg/mL) of the compound of Formula (I) to the solvent is about (1-10):1. In some embodiments of the present invention, the method for preparing the crystalline form of the present invention and the results are exemplified as follows:

| Solvent | Solid crystalline form |
|---|---|
| acetonitrile | crystalline form A |
| tetrahydrofuran | crystalline form F |
| ethyl acetate | crystalline form A |
| toluene | crystalline form A |
| chloroform | crystalline form F |

In some embodiments of the present invention, a crystalline form is prepared by a slow cooling method, comprising adding the compound of Formula (I) to a solvent, heating and stirring to dissolve the compound, allowing the resulting clear solution (the solution may be filtered as needed to provide a clear solution) to stand, and slowly cooling to afford the crystalline form.

In some embodiments, the solvent includes, but is not limited to, inorganic solvents (e.g., water) and organic solvents, such as alcohols, ketones, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), nitriles and esters having 1 to 10 carbon atoms, specifically such as isopropanol, acetone, chloroform, acetonitrile, tetrahydrofuran, methanol, n-hexane or ethyl acetate, or a mixed solvent formed by two or more of the above solvents.

In some embodiments, the slow cooling refers to, for example, a temperature-reducing rate of 0.1-0.5° C./minute, e.g., 0.1-0.3° C./minute, and preferably 0.1° C./minute. In some embodiments, the heating temperature is, for example, 30-80° C., e.g., 50° C. In some embodiments, the temperature at the end of the cooling is room temperature or 0-10° C., e.g., 5° C.

In some embodiments, the weight/volume ratio (mg/mL) of the compound of Formula (I) to the solvent is (10-50):1. In some embodiments of the present invention, the method for preparing the crystalline form of the present invention and the results are exemplified as follows:

| Solvent | Solid crystalline form |
|---|---|
| isopropanol | crystalline form B |
| tetrahydrofuran | crystalline form F |

In some embodiments of the present invention, a crystalline form is prepared by an anti-solvent addition method, comprising, but not limited to, dissolving the compound of Formula (I) in a good solvent to form a clear solution (the solution may be filtered as needed to provide a clear solution), then adding an anti-solvent thereto, and stirring (the stirring may be carried out at room temperature or under heating (e.g., heating to 30-60° C., preferably 50° C.)) to allow the precipitation of the crystalline form, or leaving the solution to stand (e.g., at room temperature) (preferably, slowly volatilizing the solvents at the same time) to allow the precipitation of the crystalline form.

In some embodiments, the good solvent includes, but is not limited to, organic solvents, such as alcohols, ketones, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), sulfones, amides and organic acids having 1 to 10 carbon atoms, such as methanol, ethanol, acetone, tetrahydrofuran, acetic acid, chloroform, dimethyl sulfoxide or dimethyl acetamide. In some embodiments, the anti-solvent includes, but is not limited to, inorganic solvents (e.g., water) and organic solvents (e.g., ketones, hydrocarbons (including alkanes, halogenated alkanes, alkenes, alkynes and aromatic hydrocarbons), ethers (including chain ethers and cyclic ethers (such as furans (including tetrahydrofurans) and dioxanes)), esters and nitriles having 1 to 10 carbon atoms), such as n-hexane, n-heptane, cyclopentyl methyl ether, acetonitrile, methyl isobutyl ketone, 2-methyltetrahydrofuran, dioxane, isopropyl acetate, dichloromethane, toluene, acetonitrile, butanone, methyl tert-butyl ether, ethyl isopropionate, dimethyl carbonate and ethyl acetate.

In some embodiments, the volume ratio of the good solvent to the anti-solvent is (0.2-1):(1-20). In some embodiments, the weight/volume ratio (mg/mL) of the compound of Formula (I) to the good solvent is (10-80):1. In some embodiments of the present invention, the method for preparing the crystalline form of the present invention and the results are exemplified as follows:

| Good solvent | Anti-solvent | Solid crystalline form |
| --- | --- | --- |
| methanol | toluene | crystalline form D |
|  | ethyl acetate | crystalline form B |
|  | cyclopentyl methyl ether | crystalline form C |
| ethanol | n-hexane | crystalline form A |
| acetone | toluene | crystalline form D |

In some embodiments of the present invention, a crystalline form is prepared by a room temperature suspension stirring method, comprising, but not limited to, adding the compound of Formula (I) to a solvent to give a suspension, stirring the suspension, followed by isolation to afford the crystalline form.

In some embodiments, the solvent includes, but is not limited to, inorganic solvents (e.g., water) and organic solvents (e.g., alcohols, ketones, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), esters, nitriles and organic acids having 1 to 10 carbon atoms, such as n-propanol, isopropanol, acetone, methyl isobutyl ketone, isopropyl acetate, acetonitrile, n-hexane, n-heptane, dichloromethane, methyl tert-butyl ether, dioxane, dimethyl carbonate, ethyl acetate, tetrahydrofuran, 2-methyltetrahydrofuran, acetic acid, toluene, chloroform, cyclopentyl methyl ether), or a mixed solvent of two or more selected from the above solvents.

In some embodiments, the weight/volume ratio (mg/mL) of the compound of Formula (I) to the solvent is (20-250):1, preferably (20-200):1, more preferably (20-150):1, and most preferably (20-100):1. In some embodiments of the present invention, the method for preparing the crystalline form of the present invention and the results are exemplified as follows:

| Solvent | Solid crystalline form |
| --- | --- |
| isopropanol | crystalline form B |
| acetone | crystalline form A |
| methyl tert-butyl ether | crystalline form A |
| isopropanol/n-hexane, 1:1 | crystalline form B |
| tetrahydrofuran/acetonitrile, 1:1 | crystalline form A |

In some embodiments of the present invention, a crystalline form is prepared by a high temperature suspension stirring method, comprising, but not limited to, adding the compound of Formula (I) to a solvent to give a suspension, stirring the suspension under heating (e.g., heated to 30-100° C., and preferably 50° C. or 80° C.), followed by isolation to afford the crystalline form.

In some embodiments, the solvent includes, but is not limited to, inorganic solvents (e.g., water) and organic solvents (e.g., alcohols, ketones, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), esters, nitriles and nitrogen-containing heterocycles having 1 to 10 carbon atoms, such as acetone, methyl isobutyl ketone, isopropyl acetate, dimethyl carbonate, dichloromethane, acetonitrile, tetrahydrofuran, 2-methyltetrahydrofuran, chloroform, n-hexane, dioxane, N-methyl pyrrolidone, cyclopentyl methyl ether, toluene and anisole).

In some embodiments, the weight/volume ratio (mg/mL) of the compound of Formula (I) to the solvent is (15-100):1, and preferably (20-100):1. In some embodiments, the heating temperature is 50-80° C. In some embodiments of the present invention, the method for preparing the crystalline form of the present invention and the results are exemplified as follows:

| Solvent | Temperature | Solid crystalline form |
| --- | --- | --- |
| isopropyl acetate | 50° C. | crystalline form A |
| dichloromethane |  | crystalline form B |
| 2-methyltetrahydrofuran |  | crystalline form D |
| water | 80° C. | crystalline form A |
| anisole |  | crystalline form D |

Definitions

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that most of the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

The word "about" as used herein refers to, as appreciated by a person skilled in the art, a range within the acceptable standard error of a value, such as ±0.05, ±0.1, ±0.2, ±0.3, ±1, ±2 or ±3, etc.

The term "solid form" as used herein includes all solid forms of the compounds of Formula (I), such as a crystalline form or amorphous form.

The term "amorphous" as used herein refers to any solid substance which lacks order in three dimensions. In some instances, amorphous solids may be characterized by known techniques, including XRPD crystallography, solid state nuclear magnet resonance (ssNMR) spectroscopy, DSC, or some combination of these techniques. As illustrated below, amorphous solids give diffuse XRPD patterns, typically comprised of one or two broad peaks (i.e., peaks having base widths of about 5° 2θ or greater).

The term "crystalline form" or "crystal" as used herein refers to any solid substance exhibiting three-dimensional order, which in contrast to an amorphous solid substance, gives a distinctive XRPD pattern with sharply defined peaks.

The term "X-ray powder diffraction pattern (XRPD pattern)" as used herein refers to the experimentally observed diffractogram or parameters derived therefrom. XRPD patterns are usually characterized by peak positions (abscissa) and peak intensities (ordinate). The XRPD pattern in the present invention is preferably collected on PANalytacal Empyrean and X'Pert3 X-ray powder diffractometer, and the transmissive mode is preferably collected on PANalytacal Empyrean X-ray powder diffractometer.

The term "2θ" as used herein refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific solid form is intended to mean the 2θ values (in degrees) as measured using the X-ray diffraction experimental conditions as described herein. For example, as described herein, Cu-Kα (Kα1 (Å): 1.540598 and Kα2 (Å): 1.544426 Å) was used as the source of radiation.

The term "differential scanning calorimetry (DSC) graph" as used herein refers to a curve recorded on a differential scanning calorimeter. The DSC graph in the present application is preferably collected on a TAQ 200/2000 differential scanning calorimeter.

As used herein, the term "essentially the same" with reference to X-ray diffraction peak positions means that typical peak position and intensity variability are taken into account. For example, one skilled in the art will appreciate that the peak positions (2θ) will show some variability, typically as much as 0.1 to 0.2 degree, as well as on the apparatus being used to measure the diffraction. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. Similarly, as used herein, "essentially the same" with reference to the DSC graph is intended to also encompass the variabilities associated with these analytical techniques, which are known to those of skill in the art. For example, a differential scanning calorimetry graph will typically have a variability of up to ±0.2° C. for well defined peaks, and even larger for broad lines (e.g., up to ±1° C.).

The liquid nuclear magnetic resonance spectrum in the present application is preferably collected on a Bruker 400M nuclear magnetic resonance spectrometer, with DMSO-d6 as the solvent, unless otherwise stated.

The polarization microscopy data in the present application is preferably collected on an Axio Lab. A1 upright microscope at room temperature.

The term "hydrocarbons" as used herein preferably means hydrocarbons having 1 to 10 carbon atoms, including alkanes, halogenated alkanes, alkenes, alkynes, and aromatic hydrocarbons, specifically including, but not limited to, dichloromethane, trichloromethane (chloroform), n-hexane, n-heptane and toluene.

The term "alcohols" as used herein preferably means alcohols having 1 to 10 carbon atoms, including, but not limited to, methanol, ethanol, 1-propanol (n-propanol), 2-propanol (isopropanol), 1-butanol, 2-butanol and tert-butanol.

The term "ethers" as used herein preferably means ethers having 2 to 6 carbon atoms, including chain ethers and cyclic ethers (e.g., furans (including tetrahydrofurans) and dioxanes), specifically including, but not limited to, diethyl ether, diisopropyl ether, methyl tert-butyl ether, tetrahydrofuran, 2-methyltetrahydrofuran, dioxane, cyclopentyl methyl ether, anisole and dimethoxyethane.

The term "nitriles" as used herein preferably means nitriles having 2 to 6 carbon atoms, including, but not limited to, acetonitrile and propionitrile.

The term "ketones solvent" as used herein preferably means ketones having 2 to 6 carbon atoms, including, but not limited to, acetone, butanone, methyl ethyl ketone, methyl isobutyl ketone, and diethyl ketone.

The term "esters" as used herein preferably means esters having 3 to 10 carbon atoms, including, but not limited to, ethyl acetate, propyl acetate, isopropyl acetate, ethyl isopropionate, dimethyl carbonate and butyl acetate.

The term "organic acids" as used herein preferably means organic acids having 1 to 10 carbon atoms, including, but not limited to, formic acid and acetic acid.

The term "sulfones" as used herein preferably means sulfones or sulfoxides having 2 to 10 carbon atoms, including, but not limited to, dimethyl sulfoxide.

The term "amides" as used herein preferably means amides having 1 to 10 carbon atoms, including, but not limited to, dimethylformamide or dimethylacetamide.

The term "nitrogen-containing heterocycles" as used herein preferably means nitrogen-containing heterocycles having 3 to 10 carbon atoms and at least one nitrogen atom, including, but not limited to, N-methylpyrrolidone.

Numerical ranges (e.g., "1 to 10") and subranges thereof (e.g., "2 to 10", "2 to 6", "3 to 10"), etc. as used herein encompass any point within the numerical range (for example, 1, 2, 3, 4, 5, 6, 7, 8, 9, or 10).

The prepared salt or crystalline form thereof may be recovered by methods including decantation, centrifugation, evaporation, gravity filtration, suction filtration, or any other technique for the recovery of solids under pressure or under reduced pressure. The recovered solid may optionally be dried. "Drying" in the present invention is carried out under reduced pressure (preferably in vacuum) until the residual solvent content is lowered within the limits given in the International Conference on Harmonisation of Technical Requirements for Registration of Pharmaceuticals for Human Use ("ICH") guidelines. The residual solvent content depends on the type of the solvent, but does not exceed about 5000 ppm, or preferably about 4000 ppm, or more preferably about 3000 ppm. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure (preferably in vacuum) for any desired period (e.g., about 1, 2, 3, 5, 10, 15, 20, 24 hours or overnight) until the desired result is achieved, as long as the salt is not degraded in quality. The drying can be carried out any desired times until the desired product quality is achieved. The dried product may optionally be subjected to a size reduction procedure to produce desired particle sizes. Milling or micronization may be performed before drying, or after the completion of drying of the product. Techniques that may be used for particle size reduction include, without limitation, ball, roller and hammer milling, and jet milling.

The term "anhydrous crystalline form" as used herein preferably means a crystalline form wherein no water molecule is comprised as a structural element.

Pharmaceutical Composition and Use thereof

In another embodiment, the present invention provides a pharmaceutical composition comprising any one or more of crystalline forms A, B, C, D, E or F of the compound of Formula (I) of the present invention and one or more pharmaceutically acceptable carriers.

In another embodiment, the present invention provides use of crystalline form A, B, C, D, E or F of the compound of Formula (I) of the present invention in the manufacture of a medicament for the prevention or treatment of an abnormal cell proliferative disease or a viral infectious disease.

In another embodiment, the present invention provides crystalline form A, B, C, D, E or F of the compound of Formula (I) of the present invention for use in the prevention or treatment of an abnormal cell proliferative disease or a viral infectious disease.

In another embodiment, the present invention provides a method for the prevention or treatment of an abnormal cell proliferative disease or a viral infectious disease, comprising administering to a subject in need thereof, preferably a mammal, a prophylactically or therapeutically effective amount of any one or more of crystalline forms A, B, C, D, E or F of the compound of Formula (I) of the present invention.

In a preferred embodiment, the abnormal cell proliferative disease includes tumors and/or cancers and related disorders in esophagus, stomach, intestine, rectum, mouth, pharynx, larynx, lung, colon, breast, uterus, endometrium, ovary, prostate, testis, bladder, kidney, liver, pancreas, bone, connective tissue, skin, eye, brain and central nervous system, as well as thyroid cancer, leukemia, Hodgkin disease, lymphoma and myeloma.

As used herein, the term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The composition of the present invention can act systemically and/or topically. To this end, it can be administered through a suitable route, such as through injection, intravenous, intraarterial, subcutaneous, intraperitoneal, intramuscular, or transdermal administration, or administered via oral, buccal, nasal, transmucosal, topical, as an ophthalmic formulation, or via inhalation.

For these routes of administration, the composition of the present invention can be administered in a suitable dosage form.

The dosage form may be solid, semi-solid, liquid, or gas formulations, specifically including, but not limited to, tablets, capsules, powders, granules, lozenges, hard candies, powders, sprays, creams, salves, suppositories, gels, pastes, lotions, ointments, aqueous suspensions, injectable solutions, suspensions, elixirs, and syrups.

The pharmaceutical composition of the present invention may be manufactured by any process well known in the art, e.g., by means of mixing, dissolving, granulating, dragee-making, levigating, emulsifying, lyophilizing processes, or the like.

As used herein, the term "therapeutically effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, and 25 mg, etc.

Unless otherwise indicated, the term "treating" or "treatment", as used herein, means reversing, alleviating, inhibiting the progress of, or preventing a disorder, condition, or disease to which such term applies, or one or more symptoms of such disorder, condition, or disease.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g., birds, amphibians, reptiles) and mammals (e.g., non-human primates, livestock and/or domesticated animals (such as sheep, dog, cat, cow, pig and the like).

Figure 1:
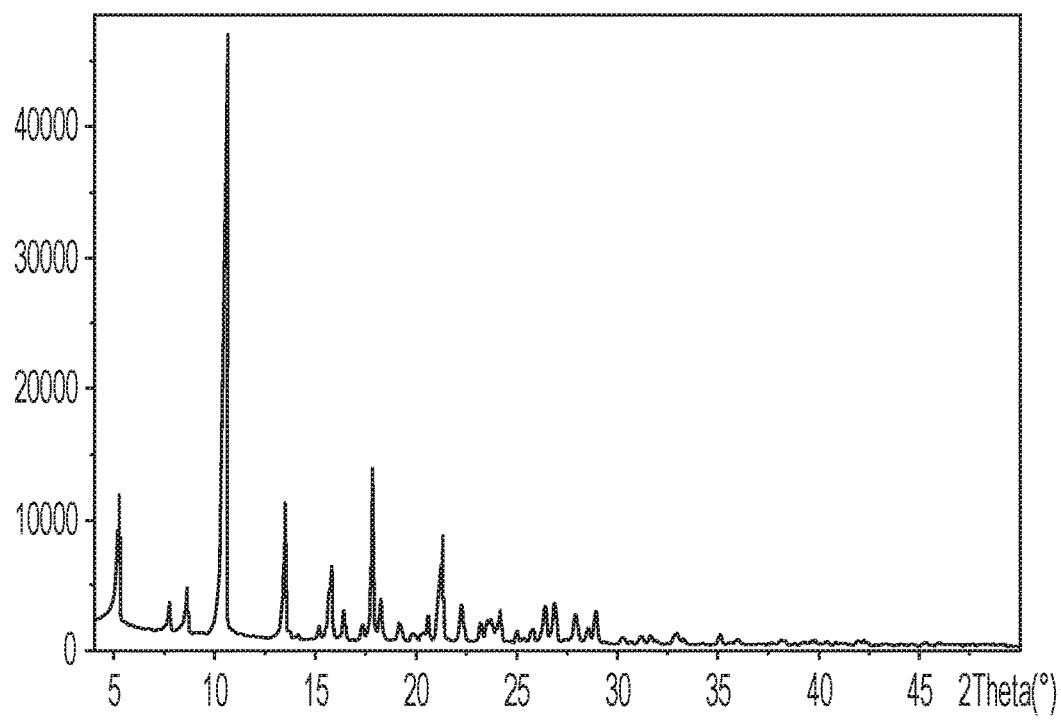
FIG. 1 is an XRPD pattern of crystalline form A of the compound of Formula (I).

The present invention is explained in more detail below with reference to the examples, which are only used to illustrate the technical solutions of the present invention, and are not intended to limit the scope thereof, and those skilled in the art may make some non-essential improvements and adjustments, which still fall within the scope of the present invention.

Example 1

Preparation of the compound of Formula (I) ((S)-isopropyl 2-(((S)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate)

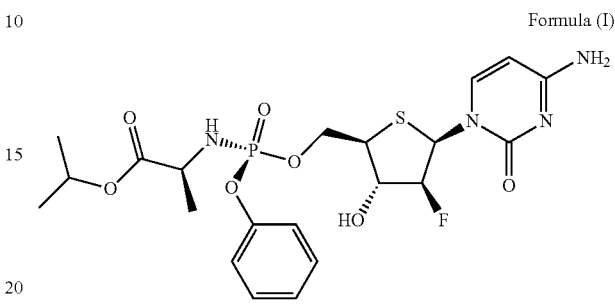

Formula (I)

(1) Preparation of 1-((2R,3S,4S,5R)-3-fluoro-4-hydroxy-5-(hydroxymethyl)tetrahydrothiophen-2-yl)cytosine (Compound A)

-continued

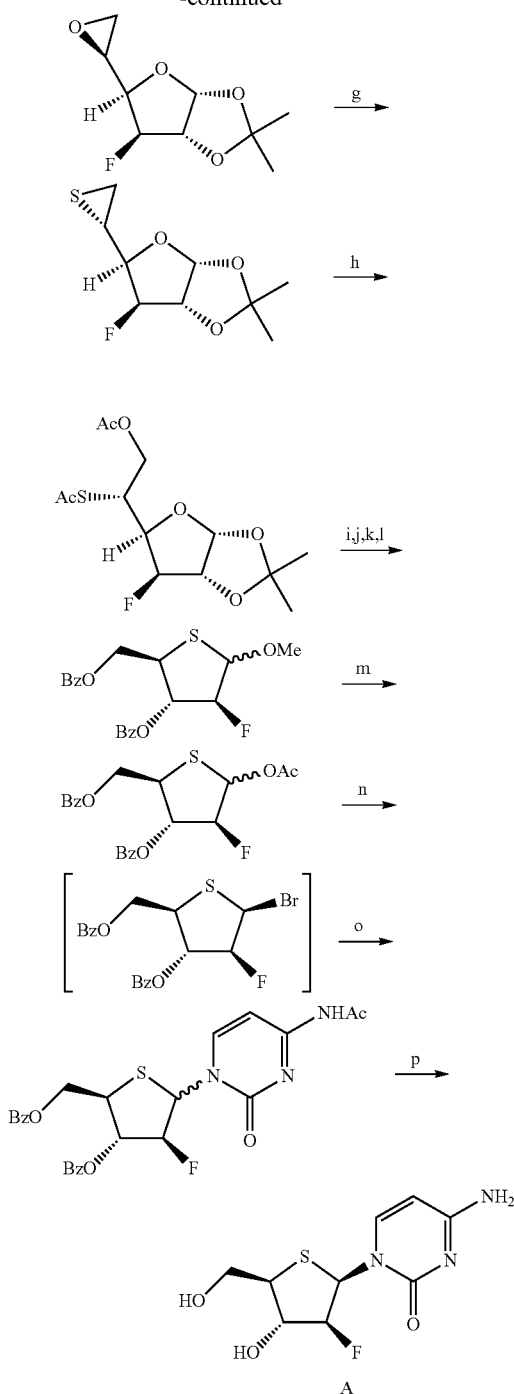

(a) SO$_2$Cl$_2$, imidazole, DCM; (b) KF, 2-methoxylethanol, reflux; (c) 2M HCl, THF; (d) BzCl, pyridine, DCM; (e) MsCl, pyridine; (f) NaOMe, MeOH; (g) thiourea, MeOH, reflux; (h) AcOK, Ac$_2$O, AcOH, reflux; (i) 90% TFA; (j) NaIO$_4$, MeOH, H$_2$O; (k) HCl, MeOH, reflux; (l) BzCl, pyridine; (m) H$_2$SO$_4$, Ac$_2$O, AcOH; (n) HBr, AcOH, DCM; (o) silylated N-acetylcytosine, 80° C.; (p) aq. NH$_3$, MeOH, HPLC separation.

Compound A employed in the present example was prepared by a method in a literature (J. Org. Chem. 1999, 64, 7912-7920).

(2) (S)-isopropyl 2-(((S)-(pentafluorophenoxy)(phenoxy)phosphoryl)amino)propanoate (Compound B)

The title compound was prepared by a method in a literature (J. Org. Chem. 2011, 76, 8311-8319), characterization data were as described in the literature.

(3) Preparation of the Compound of Formula (I)

Compound A (1 mmol) was dissolved in anhydrous tetrahydrofuran (50 mL), and air is replaced with argon for three times. Tert-Butylmagnesium chloride (1.0 mol/L, 1.2 mmol) was dropwise added at −10° C. The reaction mixture was stirred for 2 h, and reacted for 0.5 h after being warmed to room temperature. A solution of compound B (1.2 mmol) in anhydrous THF (10 mL) was dropwise added. The reaction was conducted at 30° C. for 15 h, then quenched by dropwise addition of methanol (10 mL), concentrated and purified by column chromatography, to give the compound of Formula I.
ESI-MS: 531.1 (M+1)
$^1$H NMR (DMSO-d$_6$, 400 MHz) δ 7.86 (d, J=3.4 Hz, 1H), 7.38 (t, J=7.6 Hz, 2H), 7.31-7.17 (m, 5H), 6.56 (dd, J=4 Hz, 14 Hz, 1H), 6.09-6.03 (m, 2H), 5.77 (d, J=7.6 Hz, 1H), 5.03-4.87 (m, 2H), 4.36-4.32 (m, 2H), 4.14-4.12 (m, 1H), 3.80-3.78 (m, 1H), 1.23 (d, J=6.4 Hz, 3H), 1.17 (d, J=5.2 Hz, 6H).
$^{31}$P-NMR (CD$_3$OD, 162 MHz): δ 3.29.

A single crystal of the prepared compound of Formula (I) was cultured, and subjected to X-ray single crystal diffraction, and the results indicated that the prepared compound was (S)-isopropyl 2-(((S)-(((2R,3S,4S,5R)-5-(4-amino-2-oxopyrimidin-1(2H)-yl)-4-fluoro-3-hydroxytetrahydrothiophen-2- yl)methoxy)(phenoxy)phosphoryl)amino)propanoate.

(S)-isopropyl 2-(((S)-(((2R,3S,4S,5R)-5-(4-amino-2-oxopyrimidin-1(2H)-yl)-4-fluoro-3-hydroxytetrahydrothiophen-2-yl)methoxy)(phenoxy)phosphoryl)amino)propanoate was additionally characterized, and the characterization data are as follows:
$^{31}$P-NMR (CD$_3$OD, 162 MHz): δ 3.57

Example 2: A Room Temperature Suspension Stirring Method 15.5 mg of the compound of Formula (I) was weighed and added to a 1.5 ml glass vial, 0.3 ml of acetonitrile was added, and the resulting suspension was magnetically stirred (500 rpm) at 20° C. for about 2 days, followed by centrifugation, to obtain crystalline form A.

The obtained crystalline form A was subjected to the XRPD analysis, the resulting XRPD pattern is shown in FIG. 1, and the relevant data are shown in the table below.

| 2θ (°) | Interplanar spacing (d-spacing) | Intensity % |
| --- | --- | --- |
| 5.3 | 16.8 | 29.7 |
| 7.8 | 11.3 | 5.9 |
| 8.7 | 10.2 | 8.3 |
| 10.5 | 8.4 | 100.0 |
| 13.5 | 6.6 | 21.8 |
| 15.2 | 5.8 | 1.9 |
| 15.8 | 5.6 | 12.2 |
| 16.4 | 5.4 | 4.6 |
| 17.4 | 5.1 | 2.4 |
| 17.9 | 5.0 | 27.8 |
| 18.3 | 4.9 | 6.2 |
| 19.2 | 4.6 | 2.7 |

-continued

| 2θ (°) | Interplanar spacing (d-spacing) | Intensity % |
|---|---|---|
| 19.9 | 4.5 | 1.1 |
| 20.3 | 4.4 | 0.8 |
| 20.6 | 4.3 | 3.1 |
| 21.3 | 4.2 | 18.6 |
| 22.3 | 4.0 | 5.1 |
| 23.3 | 3.8 | 2.9 |
| 23.6 | 3.8 | 3.9 |
| 24.2 | 3.7 | 11.1 |
| 25.0 | 3.6 | 1.4 |
| 25.8 | 3.5 | 2.0 |
| 26.4 | 3.4 | 5.0 |
| 26.8 | 3.3 | 6.1 |
| 27.9 | 3.2 | 4.1 |
| 28.6 | 3.1 | 2.3 |
| 28.9 | 3.1 | 4.9 |
| 30.2 | 3.0 | 1.0 |

Figure 2:
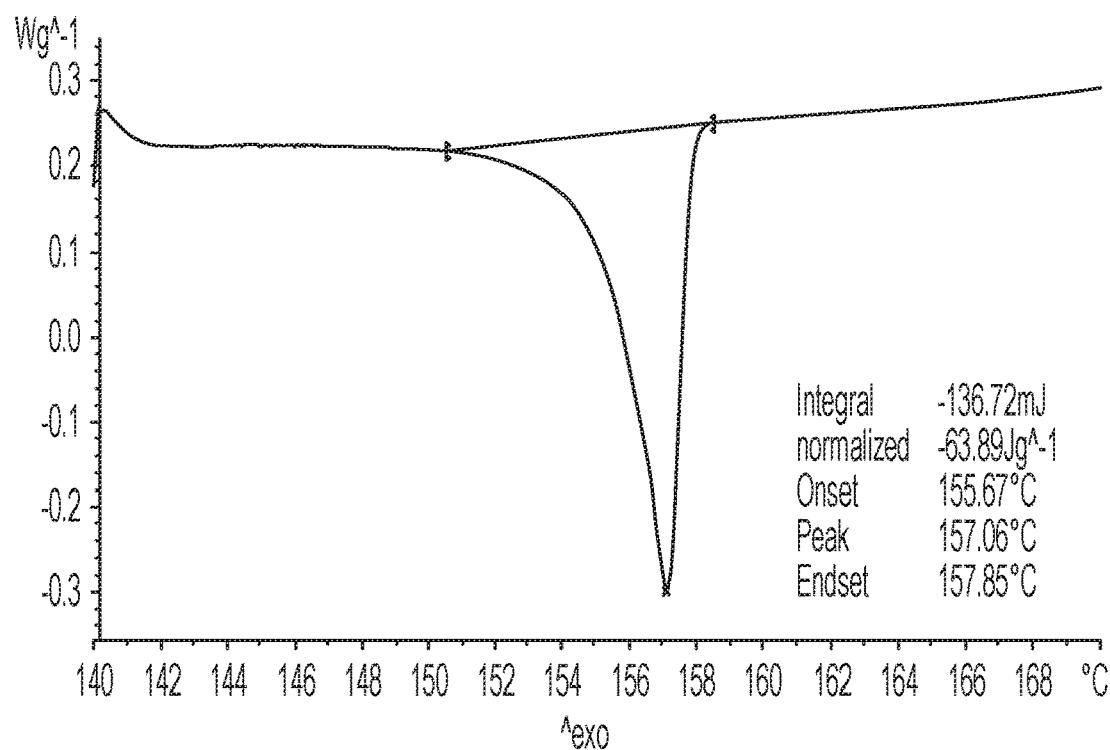
FIG. 2 is a DSC graph of crystalline form A of the compound of Formula (I).

The obtained crystalline form A was subjected to the DSC analysis, and the resulting graph is shown in FIG. 2. According to this analysis, the sample had a sharp endothermic peak at 155.67° C. (the onset temperature).

Example 3: A Gas-Solid Permeation Method

About 15 mg of the compound of Formula (I) was weighed and added to a 3 ml vial, and about 4 ml of ethyl acetate was added to another 20 ml vial. The 3 ml open vial was placed in the 20 ml vial, which was then sealed. The solid was collected after the vial was left standing at room temperature for 6 days. The XRPD pattern and the DSC graph of the obtained crystalline form were substantially the same as those in Example 2, indicating crystalline form A was obtained.

Example 4: A Room Temperature Suspension Stirring Method

About 15 mg of the compound of Formula (I) was weighed and added to a 1.5 ml glass vial, 0.2 ml of dichloromethane was added, and the resulting suspension was magnetically stirred (500 rpm) at room temperature for about 4 days, followed by centrifugation, to obtain a solid. The XRPD pattern and the DSC graph of the obtained solid were substantially the same as those in Example 2, indicating crystalline form A was obtained.

Example 5: A High Temperature Suspension Stirring Method

About 15 mg of the compound of Formula (I) was weighed and added to a 1.5 ml glass vial, 0.3 ml of water was added, and the resulting suspension was magnetically stirred (500 rpm) at 50° C. for about 4 days, followed by centrifugation, to obtain a solid. The XRPD pattern and the DSC graph of the obtained solid were substantially the same as those in Example 2, indicating crystalline form A was obtained.

Example 6: A Gas-Liquid Permeation Method

The compound of Formula (I) in the amounts as shown in the table below was weighed, dissolved in the solvents in the volumes as shown in the table below, and the supernatant was obtained by filtration, and transferred to a 3 ml vial. About 4.0 ml of the anti-solvent was added to another 20 ml vial, and the 3 ml open vial containing the supernatant was placed in the 20 ml vial. The 20 ml vial was sealed and allowed to stand at room temperature. When solid precipitation was observed, isolation was carried out to obtain crystalline form B.

Preparation of Crystalline Form B by a Gas-Liquid Permeation Method

| No. | The weight of the starting material (mg) | Good solvent | The volume of the good solvent (ml) | Anti-solvent | solid precipitation or not | Obtained crystalline form |
|---|---|---|---|---|---|---|
| 1 | 14.9 | acetone | 1.0 | methyl tert-butyl ether | Yes | crystalline form B |
| 2 | 15.4 | tetrahydrofuran | 1.0 | ethyl acetate | Yes | crystalline form B |

Figure 3:
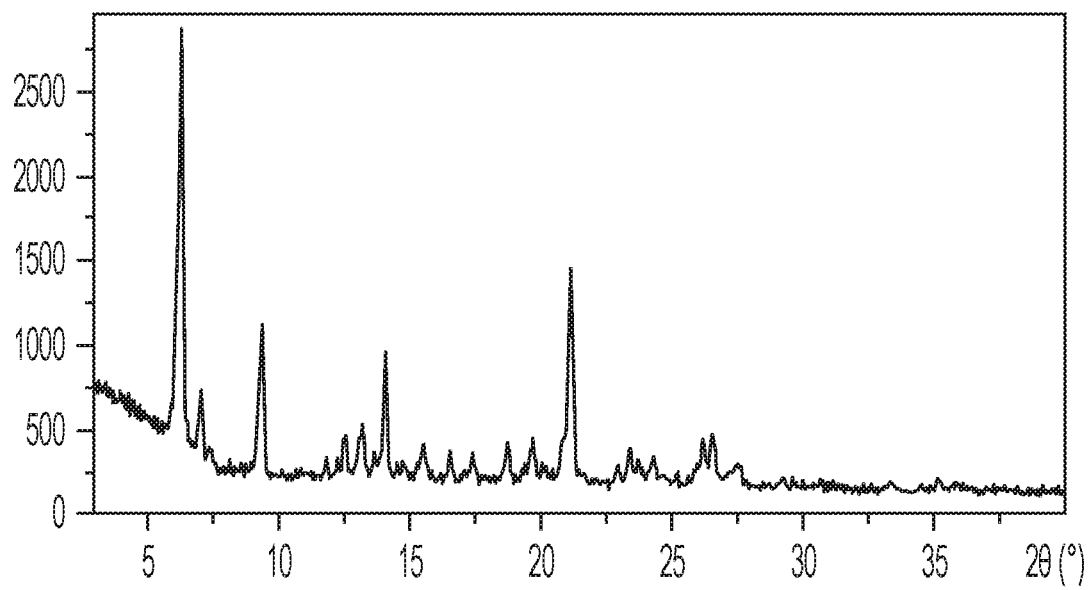
FIG. 3 is an XRPD pattern of crystalline form B of the compound of Formula (I).

The obtained crystalline form B was subjected to the XRPD analysis, the resulting XRPD pattern is shown in FIG. 3, and the relevant data are shown in the table below.

| 2θ (°) | Interplanar spacing (d-spacing) | Intensity % |
|---|---|---|
| 6.2 | 14.1 | 100.0 |
| 7.0 | 12.6 | 15.3 |
| 9.3 | 9.5 | 36.7 |
| 11.8 | 7.5 | 3.5 |
| 12.5 | 7.1 | 10.1 |
| 13.2 | 6.7 | 13.3 |
| 14.0 | 6.3 | 31.2 |
| 14.7 | 6.0 | 2.7 |
| 15.5 | 5.7 | 8.8 |
| 16.5 | 5.4 | 5.6 |
| 17.4 | 5.1 | 6.8 |
| 18.7 | 4.7 | 9.8 |
| 19.7 | 4.5 | 10.4 |
| 21.1 | 4.2 | 52.5 |
| 22.9 | 3.9 | 4.0 |
| 23.4 | 3.8 | 8.5 |
| 23.7 | 3.8 | 5.2 |
| 24.3 | 3.7 | 5.9 |
| 26.2 | 3.4 | 10.0 |
| 26.5 | 3.4 | 12.7 |
| 27.5 | 3.2 | 5.1 |
| 29.4 | 3.0 | 1.0 |
| 33.3 | 2.7 | 1.7 |
| 35.2 | 2.6 | 2.6 |

Figure 4:
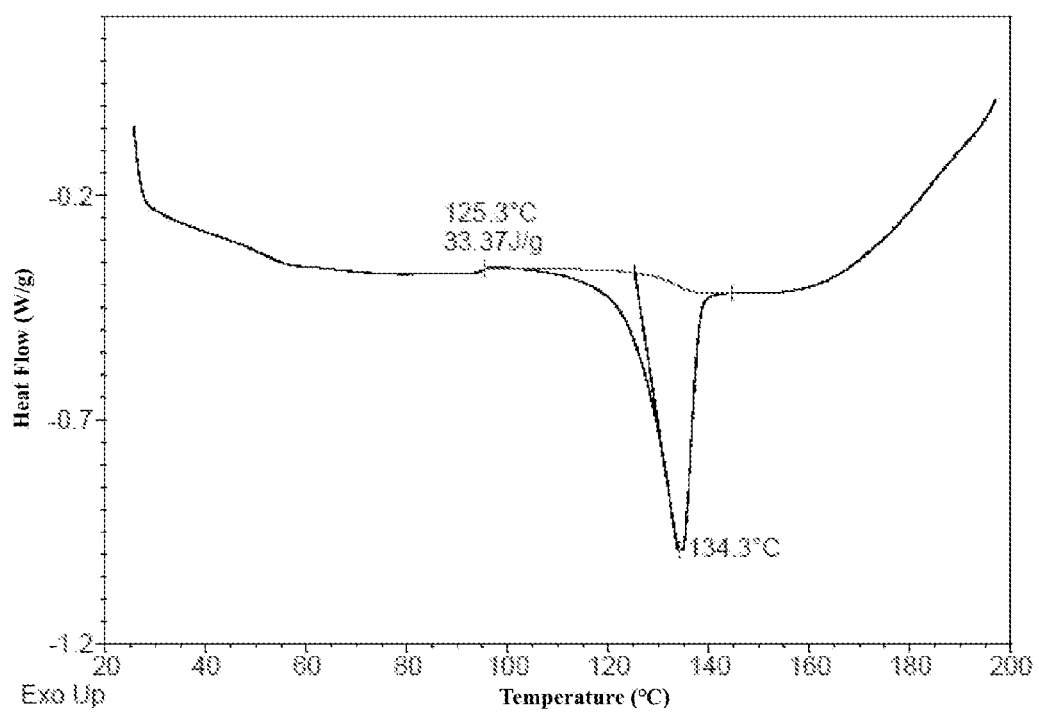
FIG. 4 is a DSC graph of crystalline form B of the compound of Formula (I).

The obtained crystalline form B was subjected to the DSC analysis, and the resulting graph is shown in FIG. 4. According to this analysis, the sample had a sharp endothermic peak at 125.3° C. (the onset temperature).

Example 7: A Slow Cooling Method 19.8 mg of the compound of Formula (I) was weighed, added to a 3 ml vial, 0.5 ml of isopropanol was added, and the solution was stirred at 50° C. for about 1 hour. Then the supernatant was obtained by filtration, and placed in a biological incubator (the incubator was cooled from 50° C. to 5° C. at a rate of 0.1° C./min, and then kept at a constant temperature of 5° C.). At that time, no solid precipitated. The solvent in the supernatant was slowly volatilized at room temperature to allow solid precipitation, and the obtained solid was isolated. The XRPD pattern and the DSC graph of the obtained solid were substantially the same as those in Example 6, indicating crystalline form B was obtained.

Example 8: A Room Temperature Slow Volatilization Method

About 15.0 mg of the compound of Formula (I) was weighed, added to a 3 ml vial, and 1.5 ml of acetone was added to form a clear solution (or obtain a clear solution after filtration). The vial containing the clear solution was sealed with parafilm on which 5 to 6 small holes were stabbed, and then left standing for slow volatilization. The resulting solid was collected. The XRPD pattern and the DSC graph of the obtained solid were substantially the same as those in Example 6, indicating crystalline form B was obtained.

Example 9: A Room Temperature Suspension Stirring Method 15.5 mg of the compound of Formula (I) was weighed, added to a 1.5-3.0 ml glass vial, 0.2 ml of isopropanol was added, and the resulting suspension was magnetically stirred (500 rpm) at room temperature for about 3~4 days before subjected to centrifugation to isolate the solid. The XRPD pattern and the DSC graph of the obtained solid were substantially the same as those in Example 6, indicating crystalline form B was obtained.

Example 10: A Room Temperature Suspension Stirring Method 235.8 mg of the compound of Formula (I) was weighed, added to a 1.5-3.0 ml glass vial, and 1.0 ml of a mixed solvent of isopropanol/n-heptane (v/v, 2:1) was added to obtain a suspension. The resulting suspension was magnetically stirred (500 rpm) at room temperature for about 3 to 4 days, and subjected to centrifugation to obtain a solid. The XRPD pattern and the DSC graph of the obtained solid were substantially the same as those in Example 6, indicating crystalline form B was obtained.

Example 11: A High Temperature Suspension Stirring Method 15.5 mg of the compound of Formula (I) was weighed and added to a 1.5 ml glass vial, 0.3 ml of dimethyl carbonate was added, and the resulting suspension was magnetically stirred (500 rpm) at 50° C. for about 4 days before subjected to centrifugation to obtain a solid. The XRPD pattern and the DSC graph of the obtained solid were substantially the same as those in Example 6, indicating crystalline form B was obtained.

Example 12: An Anti-Solvent Addition Method

The compound of Formula (I) in the amounts as shown in the table below was weighed, added to a 3 ml vial, dissolved in a corresponding amount of the good solvent shown in the table below, and filtered to a 20 ml vial. The corresponding anti-solvent shown in the table below was added dropwise to the clear solution under stirring until a solid precipitated. If no solid precipitated after adding about 10.0 ml of the anti-solvent, the clear solution was stirred at 5° C. overnight; if still no solid precipitated, the clear solution was allowed to stand at room temperature and slowly volatilized. The precipitated solid was isolated by centrifugation. The XRPD pattern and the DSC graph of the obtained solid were substantially the same as those in Example 6, indicating crystalline form B was obtained.

Preparation of Crystalline Form B by an Anti-Solvent Addition Method

| No. | The weight of the starting material (mg) | Good solvent | The volume of the good solvent (ml) | Anti-solvent | The volume of the anti-solvent (ml) | Solid precipitation or not | Obtained crystalline form |
|---|---|---|---|---|---|---|---|
| 1 | 20.0 | ethanol | 0.5 | ethyl isopropionate | 10.0 | Yes | crystalline form B |
| 2 | 15.0 | acetone | 1.0 | dimethyl carbonate | 10.0 | Yes | crystalline form B |
| 3 | 15.0 | acetone | 1.0 | n-heptane | 1.0 | Yes | crystalline form B |
| 4 | 15.0 | chloroform | 1.0 | ethyl acetate | 10.0 | Yes | crystalline form B |

Example 13: A High Polymer Induced Crystallization Method 15.0 mg of the compound of Formula (I) was weighed and added to a vial containing 1.5 ml of acetone to obtain a clear solution. Then 1.8 mg of a mixed high polymer (polyvinylpyrrolidone, polyvinyl alcohol, polyvinyl chloride, polyvinyl acetate, hydroxypropyl methylcellulose and methylcellulose mixed in equal weights) was added to the vial, and the vial was sealed with parafilm on which 5 to 6 small holes were stabbed. The vial was volatilized at room temperature to obtain a solid upon isolation. The XRPD pattern and the DSC graph of the obtained solid were substantially the same as those in Example 6, indicating crystalline form B was obtained.

Example 14: A High Polymer Induced Crystallization Method 15.0 mg of the compound of Formula (I) was weighed and added to a vial containing 1.5 ml of acetone to obtain a clear solution. Then 2.1 mg of a mixed high polymer (polycaprolactone, polyethylene glycol, polymethyl methacrylate, sodium alginate and hydroxyethyl cellulose mixed in equal weights) to the vial, and the vial was sealed with parafilm on which 5 to 6 small holes were stabbed. The vial was volatilized at room temperature to obtain a solid upon isolation. The XRPD pattern and the DSC graph of the obtained solid were substantially the same as those in Example 6, indicating crystalline form B was obtained.

Example 15: An Anti-Solvent Addition Method 20 mg of the compound of Formula (I) was weighed, added to a 3 ml vial, and dissolved in 0.5 ml of methanol. The clear solution was filtered into a 20 ml vial, and cyclopentyl methyl ether (anti-solvent) was added dropwise thereto with stirring. The final volume of the anti-solvent added was 10.0 ml, and the clear solution was stirred at room temperature for 2 hours before a solid precipitated and was centrifuged to obtain crystalline form C.

Figure 5:
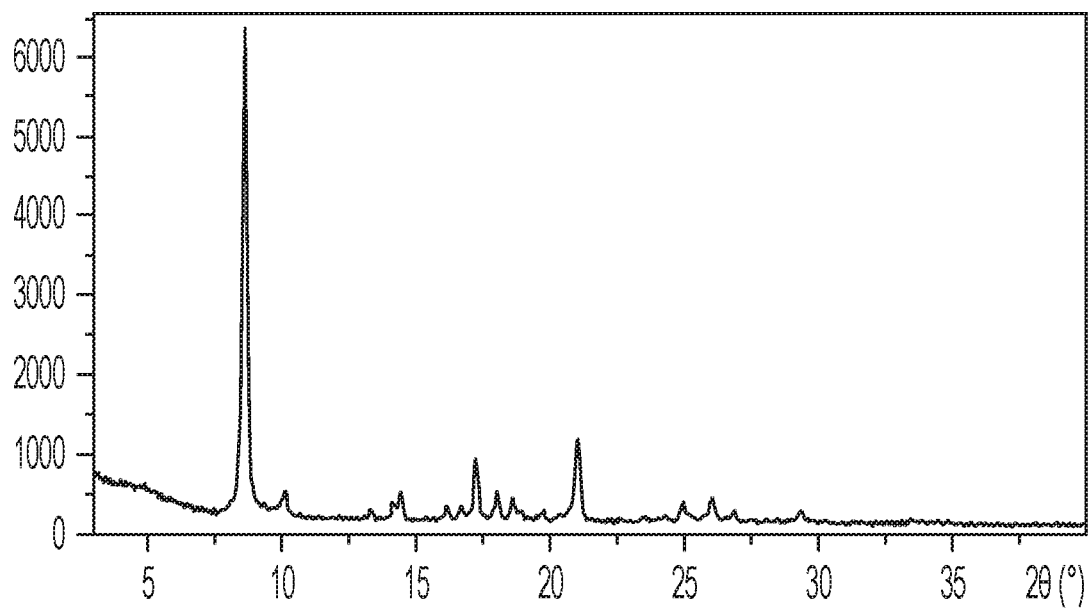
FIG. 5 is an XRPD pattern of crystalline form C of the compound of Formula (I).

The obtained crystalline form C was subjected to the XRPD analysis, the resulting XRPD pattern is shown in FIG. 5, and the relevant data are shown in the table below.

| 2θ (°) | Interplanar spacing (d-spacing) | Intensity % |
|---|---|---|
| 4.7 | 18.7 | 0.8 |
| 8.6 | 10.3 | 100.0 |
| 10.1 | 8.8 | 5.2 |
| 13.3 | 6.7 | 2.0 |
| 14.1 | 6.3 | 3.3 |
| 14.4 | 6.2 | 5.2 |
| 16.1 | 5.5 | 2.8 |
| 16.6 | 5.3 | 2.6 |
| 17.2 | 5.2 | 12.4 |
| 18.0 | 4.9 | 6.0 |
| 18.6 | 4.8 | 4.2 |
| 19.7 | 4.5 | 1.7 |
| 21.0 | 4.2 | 17.1 |
| 24.9 | 3.6 | 3.9 |
| 26.0 | 3.4 | 4.4 |
| 26.8 | 3.3 | 1.8 |
| 29.3 | 3.0 | 2.6 |

Example 16: A Room Temperature Slow Volatilization Method 14.8 mg of the compound of Formula (I) was weighed, added to a 3 ml vial, and 1.5 ml of a mixed solvent of chloroform/ethyl acetate (v/v, 3:1) was added to prepare a clear solution (or obtain a clear solution after filtration). The vial containing the clear solution was sealed with parafilm on which 5 to 6 small holes were stabbed. The vial was slowly volatilized at room temperature. Crystalline form D was collected.

Figure 6:
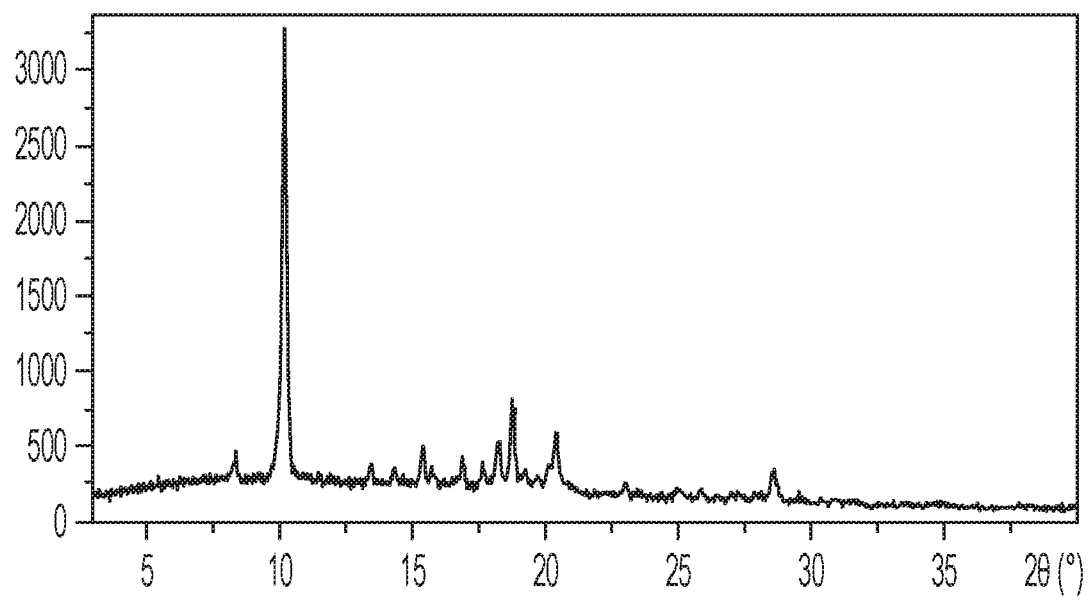
FIG. 6 is an XRPD pattern of crystalline form D of the compound of Formula (I).

The obtained crystalline form D was subjected to the XRPD analysis, the resulting XRPD pattern is shown in FIG. 6, and the relevant data are shown in the table below.

| 2θ (°) | Interplanar spacing (d-spacing) | Intensity % |
|---|---|---|
| 8.3 | 10.7 | 5.1 |
| 10.2 | 8.7 | 100.0 |
| 13.4 | 6.6 | 4.2 |
| 14.3 | 6.2 | 3.4 |
| 15.4 | 5.8 | 8.9 |
| 16.9 | 5.3 | 7.2 |
| 17.6 | 5.0 | 5.6 |
| 18.2 | 4.9 | 10.4 |
| 18.8 | 4.7 | 20.9 |
| 19.2 | 4.6 | 4.3 |
| 20.4 | 4.5 | 12.8 |
| 23.0 | 3.9 | 3.0 |
| 25.0 | 3.6 | 1.8 |
| 25.8 | 3.4 | 1.9 |
| 27.2 | 3.3 | 1.4 |
| 28.6 | 3.1 | 6.1 |
| 31.2 | 2.9 | 0.6 |

Figure 7:
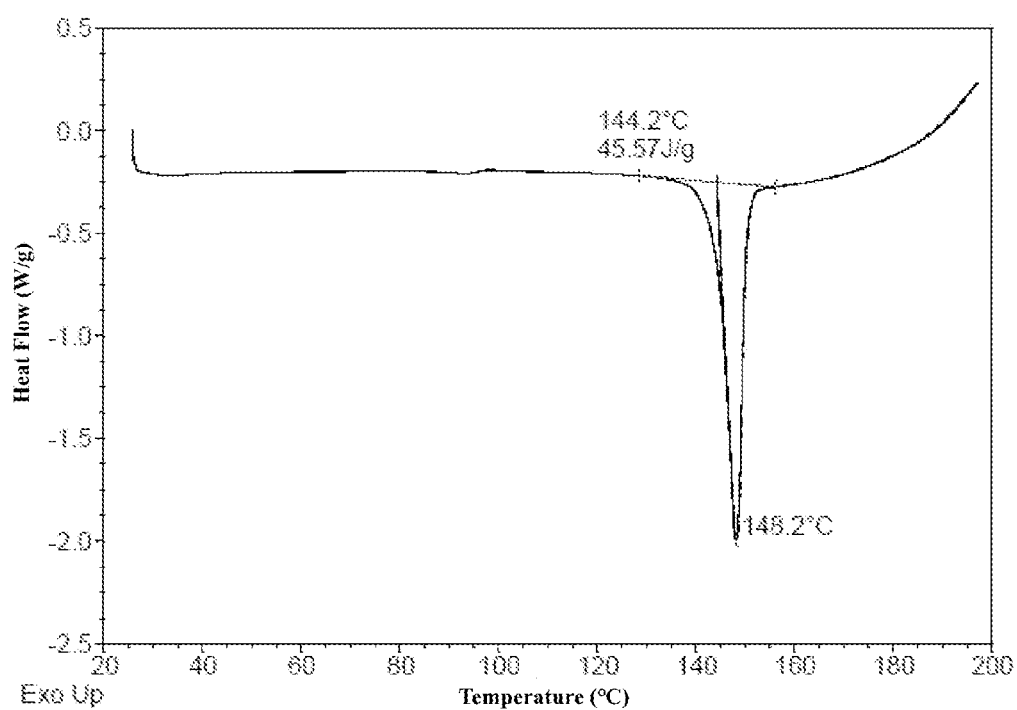
FIG. 7 is a DSC graph of crystalline form D of the compound of Formula (I).

The obtained crystalline form D was subjected to the DSC analysis, and the resulting graph is shown in FIG. 7. According to this analysis, the sample had a sharp endothermic peak at 144.2° C. (the onset temperature).

Example 17: A Room Temperature Suspension Stirring Method 235.8 mg of the compound of Formula (I) was weighed, added to a 3 ml glass vial, and 1.0 ml of 2-methyltetrahydrofuran was added thereto to obtain a suspension. The resulting suspension was magnetically stirred (500 rpm) at room temperature for about 3 days before a solid was isolated by centrifugation. The XRPD pattern and the DSC graph of the obtained solid were substantially the same as those in Example 16, indicating crystalline form D was obtained.

Example 18: An Anti-Solvent Addition Method 14.9 mg of the compound of Formula (I) was weighed, dissolved in 1.0 ml of acetone to obtain a clear solution, and 0.3 ml of 2-methyltetrahydrofuran was added to obtain a suspension. The resulting suspension was magnetically stirred (500 rpm) at 50° C. for about 4 days before a solid was isolated by centrifugation. The XRPD pattern and the DSC graph of the obtained solid were substantially the same as those in Example 16, indicating crystalline form D was obtained.

Example 19: An Anti-Solvent Addition Method 15.6 mg of the compound of Formula (I) was weighed and dissolved in 1.0 ml of acetone to obtain a clear solution. 0.3 ml of anisole was added to obtain a suspension, and the resulting suspension was magnetically stirred (500 rpm) at 80° C. for about 4 days before a solid was isolated by centrifugation. The XRPD pattern and the DSC graph of the obtained solid were substantially the same as those in Example 16, indicating crystalline form D was obtained.

Example 20: A High Temperature Suspension Stirring Method 19.1 mg of the compound of Formula (I) was weighed, added to a 1.5 ml glass vial, and then 1.0 ml of tetrahydrofuran (saturated with a sample of crystalline form A beforehand) was added to obtain a suspension. The resulting suspension was magnetically stirred (500 rpm) at 50° C. for about 1 day before crystalline form E was isolated by centrifugation.

Figure 8:
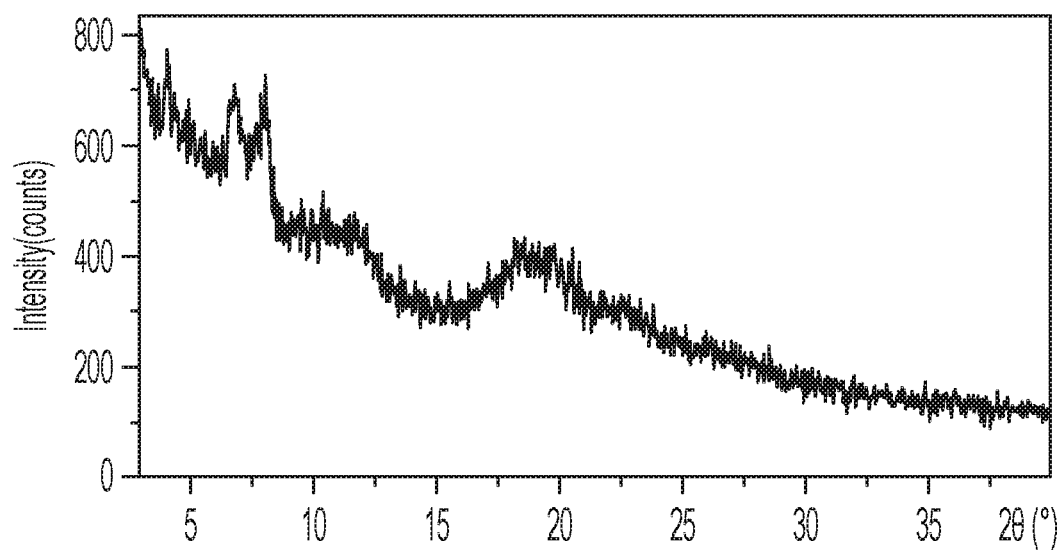
FIG. 8 is an XRPD pattern of crystalline form E of the compound of Formula (I).

The obtained crystalline form E was subjected to the XRPD analysis, the resulting XRPD pattern is shown in FIG. 8, and the relevant data are shown in the table below.

| 2θ (°) | Interplanar spacing (d-spacing) | Intensity % |
| --- | --- | --- |
| 4.0 | 21.9 | 100.0 |
| 6.8 | 13.0 | 83.9 |
| 8.0 | 11.0 | 84.9 |
| 11.6 | 7.7 | 27.8 |
| 18.6 | 4.8 | 26.8 |
| 19.8 | 4.5 | 31.3 |
| 23.8 | 3.7 | 16.2 |
| 29.6 | 3.0 | 0.5 |
| 33.9 | 2.7 | 1.1 |

Figure 9:
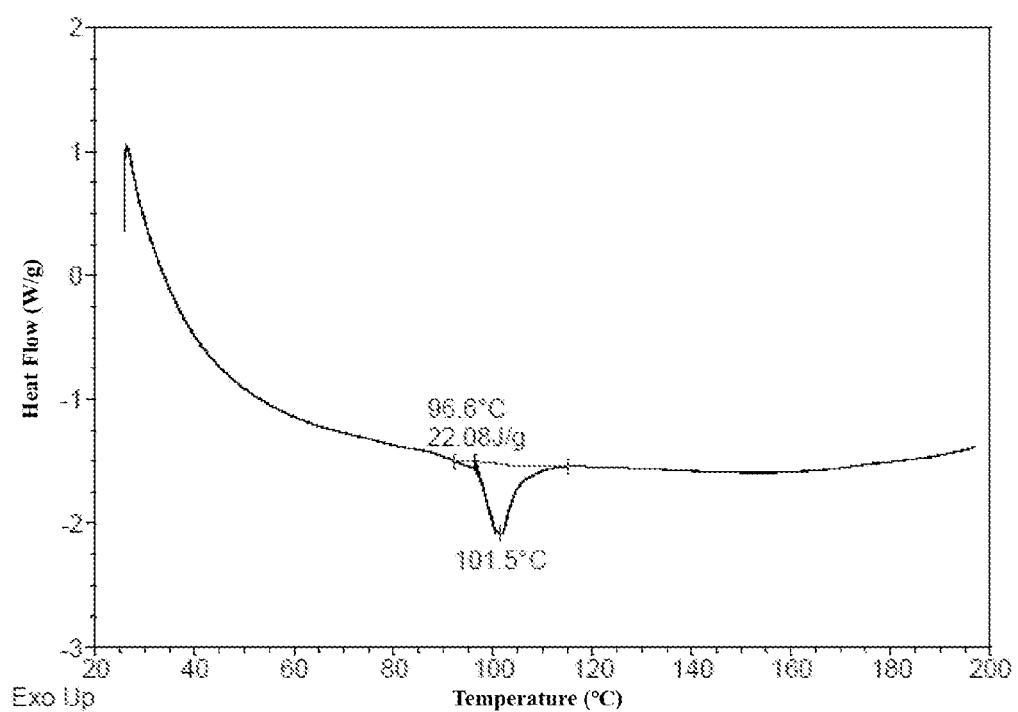
FIG. 9 is a DSC graph of crystalline form E of the compound of Formula (I).

The obtained crystalline form E was subjected to the DSC analysis, and the resulting graph is shown in FIG. 9. According to this analysis, the sample had a sharp endothermic peak at 96.6° C. (the onset temperature).

Example 21: A Room Temperature Slow Volatilization Method 65.3 mg of the compound of Formula (I) was weighed, added to a 3 ml vial, and 2.0 ml of tetrahydrofuran was added to prepare a clear solution (or obtain a clear solution after filtration). The vial containing the clear solution was sealed with parafilm on which 5 to 6 small holes were stabbed. The vial was slowly volatilized at room temperature. The resulting solid was crystalline form F.

Figure 10:
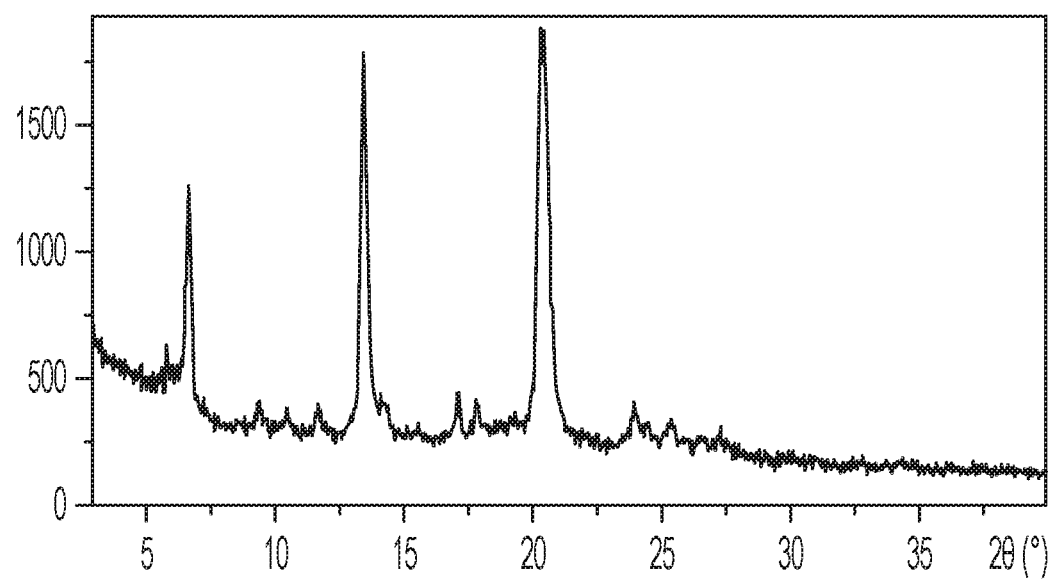
FIG. 10 is an XRPD pattern of crystalline form F of the compound of Formula (I).

The obtained crystalline form F was subjected to the XRPD analysis, the resulting XRPD pattern is shown in FIG. 10, and the relevant data are shown in the table below.

| 2θ (°) | Interplanar spacing (d-spacing) | Intensity % |
| --- | --- | --- |
| 3.1 | 28.3 | 23.9 |
| 5.8 | 15.2 | 23.0 |
| 6.7 | 13.2 | 61.8 |
| 9.4 | 9.4 | 7.9 |
| 10.5 | 8.5 | 8.0 |
| 11.7 | 7.6 | 6.6 |
| 13.5 | 6.6 | 94.9 |
| 14.2 | 6.2 | 10.1 |
| 14.9 | 6.0 | 1.8 |
| 15.6 | 5.7 | 2.3 |
| 17.1 | 5.2 | 9.1 |
| 17.8 | 5.0 | 9.3 |
| 19.3 | 4.6 | 4.9 |
| 20.4 | 4.4 | 100.0 |
| 20.5 | 4.3 | 92.4 |
| 24.0 | 3.7 | 10.3 |
| 24.5 | 3.6 | 5.5 |
| 25.4 | 3.5 | 6.6 |
| 26.5 | 3.4 | 3.9 |
| 27.3 | 3.3 | 4.4 |
| 29.1 | 3.1 | 1.2 |
| 30.9 | 2.9 | 0.6 |
| 32.7 | 2.7 | 0.7 |
| 34.3 | 2.6 | 1.7 |
| 36.2 | 2.5 | 1.0 |
| 37.1 | 2.4 | 2.4 |

Figure 11:
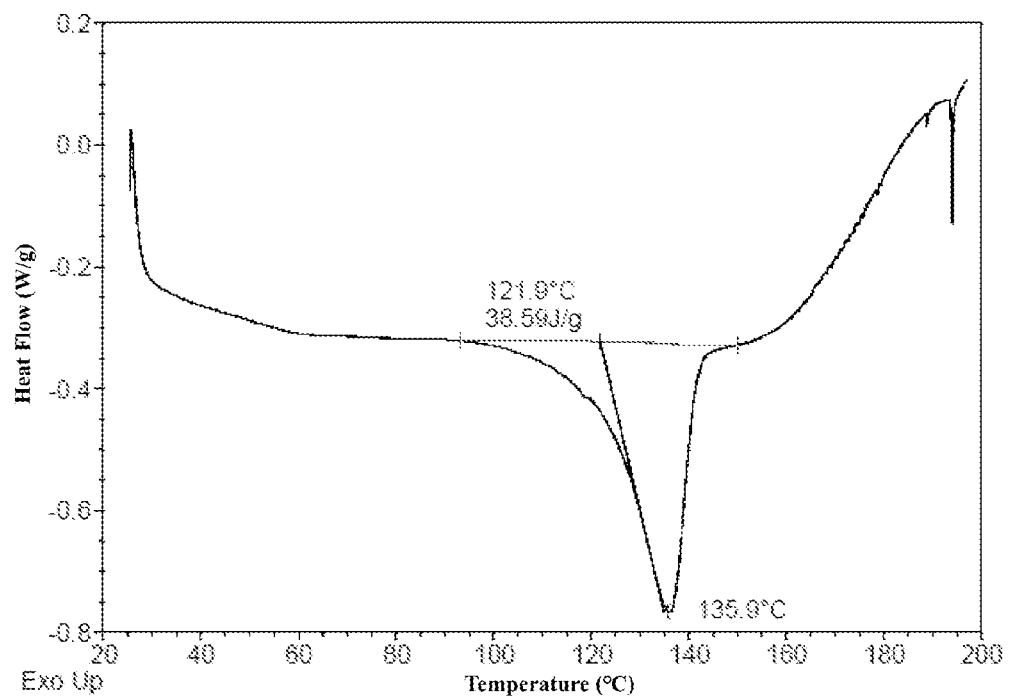
FIG. 11 is a DSC graph of crystalline form F of the compound of Formula (I).

The obtained crystalline form F was subjected to the DSC analysis, and the resulting graph is shown in FIG. 11. According to this analysis, the sample had a sharp endothermic peak at 121.9° C. (the onset temperature).

Example 22: A Slow Cooling Method 20.1 mg of the compound of Formula (I) was weighed, added to a 3 ml vial, added with 1.0 ml of tetrahydrofuran, and stirred at 50° C. for about 0.5 hour before the supernatant was collected by filtration. The resulting supernatant was placed in a biological incubator (the incubator was cooled from 50° C. to 5° C. at a rate of 0.1° C./min, and then kept at a constant temperature of 5° C.), and a solid was isolated. The XRPD pattern and the DSC graph of the obtained solid were substantially the same as those in Example 21, indicating crystalline form F was obtained.

Example 23: A Gas-Solid Permeation Method 14.8 mg of the compound of Formula (I) was weighed, added to a 3 ml vial, and about 4.0 ml of tetrahydrofuran was added to another 20 ml vial. The 3 ml open vial containing the compound of Formula (I) was placed in the 20 ml vial, which was then sealed. The solid was isolated after the vial was left standing at room temperature for 6 days. The XRPD pattern and the DSC graph of the obtained solid were substantially the same as those in Example 21, indicating crystalline form F was obtained.

Example 24: A High Polymer Induced Method 15.1 mg of the compound of Formula (I) was weighed and added to a vial containing 1.5 ml of a mixed solvent of acetonitrile/tetrahydrofuran (v/v, 1:5) to obtain a clear solution. About 2 mg of a mixed high polymer (polycaprolactone, polyethylene glycol, polymethyl methacrylate, sodium alginate and hydroxyethyl cellulose mixed in equal weights) was added to the vial, and the vial was sealed with parafilm on which 5 to 6 small holes were stabbed. The vial was volatilized at room temperature to obtain a solid upon isolation. The XRPD pattern and the DSC graph of the obtained solid were substantially the same as those in Example 21, indicating crystalline form F was obtained.

EXPERIMENTAL EXAMPLES

Experimental Example 1 Equilibrium Solubility Study

About 2.0 to 5.0 mg of each of crystalline form A, crystalline form B and crystalline form D of the compound of Formula (I) was weighed, added to a 3 ml vial, and added with 1.0 ml of deionized water. The resulting suspension was then placed in a rotary incubator (rotation speed was 25 rpm), and equilibrated in a biochemical incubator at 25° C. for 24 hours before 0.8 ml of the suspension was taken. The suspension was centrifuged (6000 rpm, 15 minutes), the supernatant was detected by HPLC for solubility, and the XRPD pattern of the solid was detected.

The test results showed that the solubility of crystalline form A and crystalline form B of the compound of Formula (I) in water at 25° C. after 24 hours were respectively about 1.0 mg/ml and 1.8 mg/ml, i.e., the solubility was good. Meanwhile, crystalline form A and crystalline form B did not undergo crystal transformation, and crystalline form D underwent crystal transformation after being dispersed in water for 24 hours.

Experimental Example 2 Solid State Stability

A suitable amount of crystalline form A of the compound of Formula (I) was weighed as a test sample, and it was left in an open container for 8 days under conditions of 40° C./75% RH (RH means relative humidity). The XRPD pattern of the test sample after the treatment was detected, and the purity was measured by HPLC.

The test results showed that crystalline form A did not undergo crystal transformation after being left in an open container for 8 days under conditions of 40° C./75% RH, and the relative purity of the sample was 99.9%. As such, crystalline form A of the compound of Formula (I) has good solid stability at 40° C./75% RH.

Experimental Example 3 Light Experiment

Crystalline form A of the compound of Formula (I) was placed under the conditions of a light intensity of 4500 1x, 25° C., and RH 25% for 30 days, and samples were taken on Day 0, 5, 11 and 30, respectively, to observe changes in the properties of the samples. The specific optical rotation was measured with a polarimeter, the loss on drying was measured, and the total impurity content was measured by HPLC.

The test results showed that after placed under the conditions of a light intensity of 4500 1x, 25° C., and RH 25% for 30 days, crystalline form A was still a white powder with no change in the appearance; the variation in the specific optical rotation during the period from Day 0 to Day 30 did not exceed 3°. The loss on drying was measured at different time points, and the loss on drying % was not greater than 1.0%; and the total impurity content detected by HPLC at different time points remained substantially unchanged.

It can be seen that crystalline form A of the compound of Formula (I) has good photostability, can guarantee the reliability of crystalline form A during storage and transportation, thereby ensuring the safety of the drug. In addition, crystalline form A does not require special packaging treatment to prevent from the influence of light, thereby reducing costs. Crystalline form A does not degrade by the influence of light, thereby improving the safety of the drug and the effectiveness upon long-term storage. A patient taking crystalline form A would not develop a photosensitivity reaction due to exposure to sunlight.

Experimental Example 4 High Temperature Experiment

Crystalline form A of the compound of Formula (I) was allowed to stand at a high temperature of 60° C. for 30 days, and samples were taken at Day 0, 5, 10, and 30, respectively, to observe changes in the properties of the samples. The specific optical rotation was measured with a polarimeter, the loss on drying was measured, and the total impurity content was measured by HPLC.

The test results showed that after standing at a high temperature of 60° C. for 30 days, crystalline form A was still a white powder with no change in the appearance; the variation in the specific optical rotation during the period from Day 0 to Day 30 did not exceed 2°. The loss on drying was measured at different time points, and the loss on drying % was not greater than 1.07%; and the total impurity content detected by HPLC at different time points remained substantially unchanged.

As such, crystalline form A of the compound of Formula (I) has good high temperature resistance (thermal stability).

Experimental Example 5 High Humidity Experiment

Crystalline form A of the compound of Formula (I) was placed under a high humidity condition of 25° C. and RH 75% for 30 days, and samples were taken at Day 0, 5, 10, and 30, respectively, to observe changes in the properties of the samples. The specific optical rotation was measured with a polarimeter, the loss on drying was measured, and the total impurity content was measured by HPLC.

The test results showed that after placed under a high humidity condition of 25° C. and RH 75% for 30 days, crystalline form A was still a white powder with no change in the appearance; the variation in the specific optical rotation during the period from Day 0 to Day 30 did not exceed 1°. The loss on drying was measured at different time points, and the loss on drying % was not greater than 1.0%; and the total impurity content detected by HPLC at different time points remained substantially unchanged.

As such, crystalline form A of the compound of Formula (I) has good high humidity resistance (i.e., high stability under a high humidity condition) and low hygroscopicity.

Crystalline form B-F of the present invention also has good high temperature resistance, high humidity resistance and/or light resistance properties.

Experimental Example 6 Stability Relationship

An equal weight of each of crystalline forms A, B and D (8 mg each) was weighed and respectively added to a $H_2O$ solution (0.3 ml) pre-saturated with a sample of crystalline form A at room temperature, and the resulting suspension was slurried at room temperature for about 4 days before isolation of the solid. The wet and dry samples were respectively subjected to XRPD pattern detection. The results showed that Both of crystalline forms B and D are converted to crystalline form A at room temperature. This indicated that crystalline form A was more stable at room temperature.

Experimental Example 7 Pharmacokinetic Experiment in Mice

Crystalline form A of the compound of Formula (I) was formulated as a suspension in 0.5% sodium carboxymethylcellulose (CMC-Na), and ICR mice were administered by single gavage to investigate the pharmacokinetic characteristics. The single gavage doses were 2 mg/kg, 4 mg/kg and 8 mg/kg, respectively. Crystalline form A, upon entering the body, rapidly metabolized as pharmacologically active metabolite I:

The Structure of Active Metabolite I:

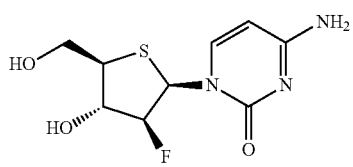 [SMILES: Nc1ccn([C@@H]2S[C@H](CO)[C@@H](O)[C@@H]2F)c(=O)n1]

The pharmacokinetic parameters were each calculated according to the concentration-time curve of metabolite I in plasma. The results are shown in Table 1:

TABLE 1

Pharmacokinetic parameters of metabolite I
after administration by single gavage to mice

| Dose (mg/kg) | $C_{max}$ (ng/mL) | $AUC_{0-\infty}$ (ng · h/mL) |
|---|---|---|
| 2 | 211 | 239 |
| 4 | 284 | 332 |
| 8 | 633 | 796 |

As can be seen from Table 1, the maximum plasma concentration ($C_{max}$) of metabolite I after administration by single gavage to mice at a dose of 2 mg/kg was 211 ng/mL, and the exposure amount ($AUC_{0-\infty}$) was 239 ng·h/mL; at a dose of 4 mg/kg, $C_{max}$ was 284 ng/mL, and $AUC_{0-\infty}$ was 332 ng·h/mL; and at a dose of 8 mg/kg, $C_{max}$ was 633 ng/mL, and $AUC_{0-\infty}$ was 796 ng·h/ml. It can be seen that the active metabolite of crystalline form A of the compound of Formula (I) of the present invention had excellent blood concentration and exposure.

Experimental Example 8 Pharmacokinetic Experiment in Beagle Dogs

Crystalline form A of the compound of Formula (I) was formulated as a suspension in 0.5% CMC-Na, and administered by single gavage to beagle dogs. The single gavage doses were 0.1 mg/kg, 0.2 mg/kg and 0.4 mg/kg, respectively. Crystalline form A, upon entering the body, rapidly metabolized as pharmacologically active metabolite I, and the pharmacokinetic parameters were each calculated according to the concentration-time curve of metabolite I in plasma. The results are shown in Table 2:

TABLE 2

Pharmacokinetic parameters of metabolite I
after administration by gavage to beagle dogs

| Dose (mg/kg) | $C_{max}$ (ng/mL) | $AUC_{0-\infty}$ (ng · h/mL) |
|---|---|---|
| 0.1 | 45.3 | 296 |
| 0.2 | 81.6 | 567 |
| 0.4 | 164 | 1120 |

As can be seen from Table 2, the maximum plasma concentration ($C_{max}$) of metabolite I after administration by single gavage to beagle dogs at a dose of 0.1 mg/kg was 45.3 ng/mL, and the exposure amount ($AUC_{0-\infty}$) was 296 ng·h/mL; at a dose of 0.2 mg/kg, $C_{max}$ was 81.6 ng/mL, and $AUC_{0-\infty}$ was 567 ng·h/mL; and at a dose of 0.4 mg/kg, $C_{max}$ was 164 ng/mL, and $AUC_{0-\infty}$ was 1120 ng·h/mL. The active metabolite of crystalline form A of the compound of Formula (I) of the present invention was shown to have excellent blood concentration and exposure.

Experimental Example 9 Drug Excretion Experiment in Mice

Crystalline form A having a radioisotope ($[^{14}C]$ crystalline form A) is formulated as a suspension in 0.5% sodium carboxymethylcellulose (CMC-Na), and ICR mice were administered by single gavage at a dose of 117 μCi/4.08 mg/kg $[^{14}C]$ crystalline form A. The absorption and excretion characteristics of crystalline form A were examined by measuring the radioactivity recovery in urine and feces.

According to the measurement, the radioactivity recovery in urine within 0 to 120 hours after intragastric administration of $[^{14}C]$ crystalline form A to mice was 78.7%. It indicated that the proportion of the drug ingredient absorbed into the blood by oral administration was at least 78.7%, that is, the absolute bioavailability of crystalline form A by intragastric administration is above 78.7%. It can be seen that crystalline form A has good oral absorption, and is suitable to be prepared as an oral formulation.

The excretion of radioactive materials after intragastric administration of $[^{14}C]$ crystalline form A to mice was mainly focused within 48 hours after administration, and the radioactive substances excreted in urine and feces within this period accounted for 84.5% of the administered amount, indicating crystalline form A excretion is complete, and the safety risk due to drug accumulation is low.

Experimental Example 10 Stability of the Pharmaceutical Composition

Conventional auxiliary materials such as an appropriate amount of cellulose powder were added to crystalline form A to prepare a mixed powder, which was stored under light (4500 lx±500 lx), high temperature (60° C.), high humidity (92.5%), respectively, for 30 days. The total impurity content in the mixed powder and the variation in dissolution rate within 30 minutes were measured, and the results are shown in the following table:

TABLE 3

Test results on the stability of a pharmaceutical composition

| Tested item | Day 0 | light 4500 lx ± 500 lx 30 days | high temperature 60° C. 30 days | high humidity 92.5% 30 days |
|---|---|---|---|---|
| total impurity content (%) | 0.4 | 0.5 | 0.9 | 0.6 |
| dissolution rate (%) | 97.1 | 97.5 | 93.4 | 96.7 |

The results showed that after the mixed powder prepared with crystalline form A and conventional auxiliary materials was stored under the conditions of light, high temperature (60° C.) and high humidity (92.5%), respectively, for 30 days, the total impurity contents were all kept below 0.9%, and the dissolution rates were maintained above 93% within 30 minutes. It was confirmed that crystalline form A is suitable to be prepared as a pharmaceutical composition having good stability and dissolution properties. Other crystalline forms of the present invention also had good composition stability.

Experimental Example 11 Powder Properties of a Pharmaceutical Composition

Crystalline form A and microcrystalline cellulose were mixed at a weight ratio of 1:3, and then the angle of repose of the mixed powder was measured by a fixed funnel method. Specifically, a funnel was fixed at a certain height (H), and the mixed powder was placed in the funnel and allowed to naturally flow down into a pile until the tip of the circular cone just reached the funnel outlet. The radius (r) of the conical bottom surface was measured, the angle of repose was calculated. Angle of repose=arc tg (H/r).

The results showed that the angle of repose of the mixed powder was in the range of 36-40 degrees, which confirmed that the powder formed by mixing crystalline form A and conventional auxiliary materials had good fluidity, can meet the requirements on fluidity of a mixed powder of raw and auxiliary materials in production, and is suitable for industrial production of a pharmaceutical composition. Other crystalline forms of the present invention also had good powder properties.

The above specific embodiments describe the present invention in further detail. However, the scope of the above-mentioned subject matter of the present invention should not be construed as being limited to the above examples, and the technical solutions implemented based on the disclosure of the present invention are all within the scope of the present invention.

What is claimed is:

1. Crystalline form A of the compound of Formula (I):

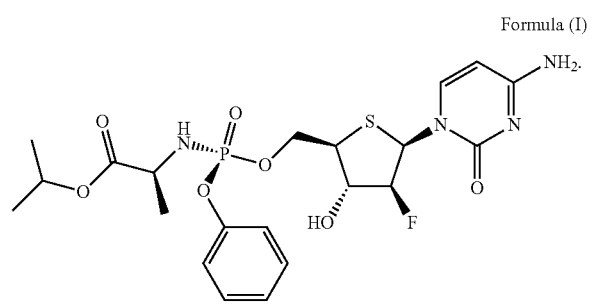 [SMILES: CC(C)OC(=O)[C@H](C)N[P@](=O)(OC[C@H]1S[C@@H](n2ccc(N)nc2=O)[C@@H](F)[C@@H]1O)Oc1ccccc1]

Formula (I)

wherein the crystalline form A has an XRPD pattern comprising characteristic peaks at diffraction angles (2θ) of 10.5±0.2°, 13.5±0.2° and 17.9±0.2°.

2. A pharmaceutical composition comprising crystalline form A of the compound of Formula (I) according to claim 1 and one or more pharmaceutically acceptable carriers.

3. The crystalline form A according to claim 1, wherein the crystalline form A has an XRPD pattern comprising characteristic peaks at diffraction angles (2θ) of 10.5±0.2°, 13.5±0.2°, 15.8±0.2°, 17.9±0.2°, 18.3±0.2° and 21.3±0.2°.

4. A pharmaceutical composition comprising crystalline form A of the compound of Formula (I) according to claim 3 and one or more pharmaceutically acceptable carriers.

5. The crystalline form A according to claim 1, wherein the crystalline form A has an XRPD pattern comprising characteristic peaks at diffraction angles (2θ) of 10.5±0.2°, 13.5±0.2°, 15.8±0.2°, 17.9±0.2°, 18.3±0.2°, 21.3±0.2°, 22.3±0.2°, 24.2±0.2° and 26.8±0.2°.

6. A pharmaceutical composition comprising crystalline form A of the compound of Formula (I) according to claim 5 and one or more pharmaceutically acceptable carriers.

7. A method for the preparation of crystalline form A of the compound of Formula (I) according to claim 1, selected from the group consisting of a gas-solid permeation method, an anti-solvent addition method, a room temperature slow volatilization method, a room temperature suspension stirring method and a high temperature suspension stirring method.

8. A method for the treatment of an abnormal cell proliferative disease or a viral infectious disease, comprising administering to a subject in need thereof the crystalline form A according to claim 1.

9. A crystalline form of the compound of Formula (I):

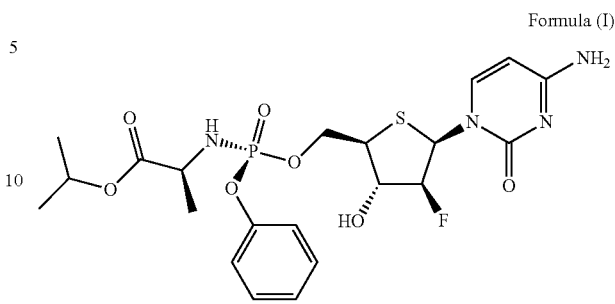

Formula (I)

wherein the crystalline form of the compound of Formula (I) is selected from the group consisting of crystalline form B having an XRPD pattern comprising characteristic peaks at diffraction angles (2θ) of 7.0±0.2°, 14.0±0.2° and 21.1±0.2°;

crystalline form C having an XRPD pattern comprising characteristic peaks at diffraction angles (2θ) of 8.6±0.2°, 17.2±0.2° and 21.0±0.2°;

crystalline form D having an XRPD pattern comprising characteristic peaks at diffraction angles (2θ) of 10.2±0.2°, 18.8±0.2° and 20.4±0.2°;

crystalline form E having an XRPD pattern comprising characteristic peaks at diffraction angles (2θ) of 4.0±0.2°, 6.8±0.2° and 8.0±0.2°; and crystalline form F having an XRPD pattern comprising characteristic peaks at diffraction angles (2θ) of 6.7±0.2°, 13.5±0.2° and 20.4±0.2°.

10. A pharmaceutical composition comprising crystalline form B of the compound of Formula (I) according to claim 9 and one or more pharmaceutically acceptable carriers.

11. A pharmaceutical composition comprising crystalline form C of the compound of Formula (I) according to claim 9 and one or more pharmaceutically acceptable carriers.

12. A pharmaceutical composition comprising crystalline form D of the compound of Formula (I) according to claim 9 and one or more pharmaceutically acceptable carriers.

13. A pharmaceutical composition comprising crystalline form E of the compound of Formula (I) according to claim 9 and one or more pharmaceutically acceptable carriers.

14. A pharmaceutical composition comprising crystalline form F of the compound of Formula (I) according to claim 9 and one or more pharmaceutically acceptable carriers.

15. The crystalline form according to claim 9,
wherein the crystalline form of the compound of Formula (I) is selected from the group consisting of crystalline form B having an XRPD pattern comprising characteristic peaks at diffraction angles (2θ) of 6.2±0.2°, 7.0±0.2°, 13.2±0.2°, 14.0±0.2°, 21.1±0.2° and 26.2±0.2°;

crystalline form C having an XRPD pattern comprising characteristic peaks at diffraction angles (2θ) of 8.6±0.2°, 10.1±0.2°, 14.4±0.2°, 17.2±0.2°, 18.0±0.2° and 21.0±0.2°;

crystalline form D having an XRPD pattern comprising characteristic peaks at diffraction angles (2θ) of 10.2±0.2°, 15.4±0.2°, 16.9±0.2°, 18.2±0.2°, 18.8±0.2° and 20.4±0.2°;

crystalline form E having an XRPD pattern comprising characteristic peaks at diffraction angles (2θ) of 4.0±0.2°, 6.8±0.2°, 8.0±0.2°, 11.6±0.2°, 18.6±0.2° and 19.8±0.2°; and crystalline form F having an XRPD pattern comprising characteristic peaks at diffraction angles (2θ) of 5.8±0.2°, 6.7±0.2°, 13.5±0.2°, 14.2±0.2°, 17.8±0.2° and 20.4±0.2°.

16. A pharmaceutical composition comprising the crystalline form of the compound of Formula (I) according to claim 15 and one or more pharmaceutically acceptable carriers.

17. The crystalline form according to claim 9,
wherein the crystalline form of the compound of Formula (I) is selected from the group consisting of
crystalline form B having an XRPD pattern comprising characteristic peaks at diffraction angles (2θ) of 6.2±0.2°, 7.0±0.2°, 9.3±0.2°, 13.2±0.2°, 14.0±0.2°, 15.5±0.2°, 18.7±0.2°, 21.1±0.2° and 26.2±0.2°;
crystalline form C having an XRPD pattern comprising characteristic peaks at diffraction angles (2θ) of 8.6±0.2°, 10.1±0.2°, 14.4±0.2°, 17.2±0.2°, 18.0±0.2°, 18.6±0.2°, 21.0±0.2°, 24.9±0.2° and 26.0±0.2°;
crystalline form D having an XRPD pattern comprising characteristic peaks at diffraction angles (2θ) of 10.2±0.2°, 14.3±0.2°, 15.4±0.2°, 16.9±0.2°, 18.2±0.2°, 18.8±0.2°, 20.4±0.2°, 25.0±0.2° and 28.6±0.2°;
crystalline form E having an XRPD pattern comprising characteristic peaks at diffraction angles (2θ) of 4.0±0.2°, 6.8±0.2°, 8.0±0.2°, 11.6±0.2°, 18.6±0.2°, 19.8±0.2°, 23.8±0.2°, 29.6±0.2° and 33.9±0.2°; and
crystalline form F having an XRPD pattern comprising characteristic peaks at diffraction angles (2θ) of 5.8±0.2°, 6.7±0.2°, 9.4±0.2°, 11.7±0.2°, 13.5±0.2°, 14.2±0.2°, 17.8±0.2°, 20.4±0.2° and 27.3±0.2°.

18. A pharmaceutical composition comprising the crystalline form of the compound of Formula (I) according to claim 17 and one or more pharmaceutically acceptable carriers.

19. A method for the preparation of crystalline form B of the compound of Formula (I) according to claim 9, selected from the group consisting of a gas-liquid permeation method, a slow cooling method, a room temperature slow volatilization method, a room temperature suspension stirring method, a high temperature suspension stirring method, an anti-solvent addition method and a high polymer induced crystallization method.

20. A method for the preparation of crystalline form C of the compound of Formula (I) according to claim 9, wherein the method is an anti-solvent addition method, comprising dissolving the compound of Formula (I) in a good solvent to form a clear solution, then adding an anti-solvent thereto, and stirring to allow the precipitation of crystalline form C, or volatilizing the solvents to allow the precipitation of crystalline form C.

21. A method for the preparation of crystalline form D of the compound of Formula (I) according to claim 9, selected from the group consisting of an anti-solvent addition method, a room temperature slow volatilization method, a room temperature suspension stirring method and a high temperature suspension stirring method.

22. A method for the preparation of crystalline form E of the compound of Formula (I) according to claim 9, wherein the method is a high temperature suspension stirring method, comprising adding the compound of Formula (I) to a solvent to give a suspension, stirring the suspension under heating, followed by isolation to afford crystalline form E.

23. A method for the preparation of crystalline form F of the compound of Formula (I) according to claim 9, selected from the group consisting of a room temperature slow volatilization method, a slow cooling method, a gas-solid permeation method and a high polymer induced crystallization method.

24. A method for the treatment of an abnormal cell proliferative disease or a viral infectious disease, comprising administering to a subject in need thereof the crystalline form B according to claim 9.

25. A method for the treatment of an abnormal cell proliferative disease or a viral infectious disease, comprising administering to a subject in need thereof the crystalline form C according to claim 9.

26. A method for the treatment of an abnormal cell proliferative disease or a viral infectious disease, comprising administering to a subject in need thereof the crystalline form D according to claim 9.

\* \* \* \* \*